(12) United States Patent
Rapoport

(10) Patent No.: US 10,078,122 B2
(45) Date of Patent: Sep. 18, 2018

(54) MRI RF SHIELDING JACKET

(71) Applicant: Aspect Imaging Ltd., Shoham (IL)

(72) Inventor: Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 634 days.

(21) Appl. No.: 14/623,051

(22) Filed: Feb. 16, 2015

(65) Prior Publication Data

US 2015/0253401 A1 Sep. 10, 2015

Related U.S. Application Data

(60) Provisional application No. 61/950,125, filed on Mar. 9, 2014.

(30) Foreign Application Priority Data

Mar. 11, 2014 (DE) .................. 20 2014 101 102

(51) Int. Cl.
*G01V 3/00* (2006.01)
*G01R 33/422* (2006.01)
*A61B 5/055* (2006.01)
*G01R 33/38* (2006.01)
*G01R 33/48* (2006.01)

(52) U.S. Cl.
CPC ............ *G01R 33/422* (2013.01); *A61B 5/055* (2013.01); *G01R 33/3804* (2013.01); *G01R 33/48* (2013.01); *A61B 2560/04* (2013.01); *Y10T 29/49016* (2015.01)

(58) Field of Classification Search
None
See application file for complete search history.

(56) References Cited

U.S. PATENT DOCUMENTS

| 3,534,251 | A | 10/1970 | Richards |
| 4,910,461 | A | 3/1990 | Van Vaals |
| 4,977,585 | A | 12/1990 | Boyd |
| 5,028,872 | A | 7/1991 | Nakabayashi |

(Continued)

FOREIGN PATENT DOCUMENTS

| DE | 202013105276 | 2/2014 |
| EP | 0825450 | 8/1997 |

(Continued)

OTHER PUBLICATIONS

Hart et al, "Segmented and shielded structures for reduction of thermal expansion-induced tilt errors," Precision Engineering, vol. 28, Issue 4, Oct. 2004, pp. 1-6.*

(Continued)

*Primary Examiner* — Louis Arana
(74) *Attorney, Agent, or Firm* — Pearl Cohen Zedek Latzer Baratz LLP

(57) ABSTRACT

A jacket for radio frequency (RF) shielding a Magnetic Resonance Device (MRD) from external environment electromagnetic interference during its operation, which allows for homogenized imaging conditions. The RF shielding jacket is sized and shaped like an envelope to accommodate the MRD, with at least a portion of the RF shielding jacket including an electromagnetic interference shield. The RF shielding jacket is also combined with passive temperature insulating properties.

19 Claims, 12 Drawing Sheets

(56) References Cited

U.S. PATENT DOCUMENTS

| | | | |
|---|---|---|---|
| 5,039,826 A | 8/1991 | Newland | |
| 5,065,760 A | 11/1991 | Krause et al. | |
| 5,159,929 A | 11/1992 | Morris et al. | |
| 5,243,286 A | 9/1993 | Rzedzian et al. | |
| 5,304,932 A | 4/1994 | Carlson | |
| 5,305,749 A | 4/1994 | Li et al. | |
| 5,572,131 A | 11/1996 | Rzedzian | |
| 5,594,200 A | 1/1997 | Ramsey | |
| 5,635,889 A | 6/1997 | Stelter | |
| 5,986,531 A | 11/1999 | Carrozzi | |
| RE36,679 E | 5/2000 | Zakhor et al. | |
| 6,188,015 B1 * | 2/2001 | Curran, Sr. | H05K 9/0003 174/353 |
| 6,215,309 B1 | 4/2001 | Rzedzian et al. | |
| 6,346,814 B1 | 2/2002 | Carrozzi et al. | |
| 6,546,814 B1 | 4/2003 | Choe et al. | |
| 6,711,430 B1 | 3/2004 | Ferris et al. | |
| 6,801,038 B2 | 10/2004 | Carrozzi et al. | |
| 6,873,156 B2 | 3/2005 | Ferris et al. | |
| 6,995,562 B2 | 2/2006 | Laskaris et al. | |
| 7,141,974 B2 | 11/2006 | Edelstein et al. | |
| 7,157,911 B2 | 1/2007 | Suzuki et al. | |
| 7,171,256 B1 | 1/2007 | Graessle et al. | |
| 7,375,526 B2 | 5/2008 | Edelstein et al. | |
| 7,529,575 B2 | 5/2009 | Rezzonico et al. | |
| 7,633,294 B2 | 12/2009 | Leussler et al. | |
| 7,715,895 B1 | 5/2010 | Graessle et al. | |
| 7,772,503 B2 | 8/2010 | Ginanneschi | |
| 7,801,613 B2 | 9/2010 | Li et al. | |
| 8,851,018 B2 | 10/2014 | Rapoport et al. | |
| 8,896,310 B2 | 11/2014 | Rapoport | |
| 9,301,724 B2 | 4/2016 | McKnight et al. | |
| 9,498,167 B2 | 11/2016 | Mostafavi et al. | |
| 9,562,956 B2 | 2/2017 | Rapoport | |
| 2002/0057088 A1 | 5/2002 | Carrozzi et al. | |
| 2003/0016518 A1 * | 1/2003 | Arz | G01R 33/422 361/818 |
| 2003/0058502 A1 | 3/2003 | Griffiths et al. | |
| 2003/0088175 A1 | 5/2003 | Branch et al. | |
| 2005/0046422 A1 | 3/2005 | Edelstein et al. | |
| 2005/0049491 A1 | 3/2005 | Rezzonico et al. | |
| 2007/0026733 A1 | 2/2007 | Greim et al. | |
| 2007/0135704 A1 | 6/2007 | Branch et al. | |
| 2007/0232894 A1 | 10/2007 | Feenan | |
| 2008/0060843 A1 | 3/2008 | Ginanneschi | |
| 2008/0094062 A1 | 4/2008 | Edelstein et al. | |
| 2008/0186026 A1 | 8/2008 | Leussler et al. | |
| 2010/0000780 A1 | 1/2010 | Zhu et al. | |
| 2011/0162652 A1 | 3/2011 | Rapoport | |
| 2011/0186049 A1 | 3/2011 | Rapoport | |
| 2011/0234347 A1 | 9/2011 | Rapoport | |
| 2011/0304333 A1 | 12/2011 | Rapoport | |
| 2012/0046722 A1 | 2/2012 | Olsen et al. | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0118630 A1 | 5/2012 | Jiang et al. | |
| 2012/0119742 A1 | 5/2012 | Rapoport | |
| 2013/0079624 A1 | 3/2013 | Rapoport | |
| 2013/0109956 A1 | 5/2013 | Rapoport | |
| 2013/0237803 A1 | 5/2013 | Rapoport | |
| 2013/0229181 A1 | 9/2013 | Biber et al. | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport | |
| 2014/0103927 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport | |
| 2014/0300358 A1 | 10/2014 | Rapoport | |
| 2014/0354279 A1 | 12/2014 | Dumoulin et al. | |
| 2014/0364722 A1 | 12/2014 | Dumoulin | |
| 2014/0378821 A1 | 12/2014 | Rapoport et al. | |
| 2014/0378825 A1 | 12/2014 | Rapoport et al. | |
| 2015/0059655 A1 | 3/2015 | Rapoport | |
| 2015/0065788 A1 | 3/2015 | Rapoport | |
| 2015/0112186 A1 | 4/2015 | Rapoport et al. | |
| 2015/0137812 A1 | 5/2015 | Rapoport | |
| 2015/0141799 A1 | 5/2015 | Rapoport et al. | |
| 2015/0168519 A1 | 6/2015 | Rapoport | |
| 2015/0208994 A1 | 7/2015 | Rapoport | |
| 2015/0212172 A1 | 7/2015 | Rapoport | |
| 2015/0212173 A1 | 7/2015 | Rapoport | |
| 2015/0253400 A1 | 9/2015 | Rapoport | |
| 2015/0253401 A1 | 9/2015 | Rapoport | |
| 2017/0146619 A1 | 5/2017 | Strauss et al. | |
| 2017/0256853 A1 | 9/2017 | Anderson et al. | |

FOREIGN PATENT DOCUMENTS

| | | |
|---|---|---|
| JP | 62207448 | 9/1987 |
| JP | 2005270422 | 10/2005 |
| WO | WO2000/016116 | 3/2000 |
| WO | WO2015071906 | 5/2015 |

OTHER PUBLICATIONS

Aspect Imaging Ltd., "Shutting Assembly for Closing an Entrance of an MRI Device", co-pending U.S. Appl. No. 14/540,163, filed Nov. 13, 2014.

Aspect Imaging Ltd, "MRI—Incubator's Closure Assembly", co-pending U.S. Appl. No. 14/539,442, filed Nov. 12, 2014.

Aspect Imaging Ltd., "Cage in an MRD with a Fastening/Attenuating System", co-pending U.S. Appl. No. 14/527,950, filed Oct. 30, 2014.

Rapoport, Uri, "RF Shielding Conduit in an MRI Closure Assembly", co-pending U.S. Appl. No. 14/574,785, filed Dec. 18, 2014.

Aspect Imaging Ltd., "System and Method for Generating Invasively Hyperpolarized Images", co-pending U.S. Appl. No. 14/556,682, filed Dec. 1, 2014.

Aspect Imaging Ltd., "System and Method for Generating Invasively Hyperpolarized Images", co-pending U.S. Appl. No. 14/556,654, filed Dec. 1, 2014.

Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.

Aspect Imaging Ltd., "Chamber for Housing Animals During Anaesthetic Procedures", co-pending U.S. Appl. No. 14/537,266, filed Nov. 10, 2014.

Aspect Imaging Ltd., "RF Automated Tuning System Used in a Magnetic Resonance Device and Methods Thereof", co-pending U.S. Appl. No. 14/588,741, filed Jan. 2, 2015.

Aspect Imaging Ltd., "Means and Method for Operating an MRI Device Within a RF-Magnetic Environment", co-pending U.S. Appl. No. 14/596,329, filed Jan. 14, 2015.

Aspect Imaging Ltd., "Means and Method for Operating an MRI Device Within a RF-Magnetic Environment", co-pending U.S. Appl. No. 14/596,329, filed Jan. 14, 2015

Aspect Imaging Ltd., "CT/MRI Integrated System for the Diagnosis of Acute Strokes and Methods Thereof", co-pending U.S. Appl. No. 14/598,517, filed Jan. 16, 2015.

Aspect Imaging Ltd., "Mechanical Clutch for MRI", co-pending U.S. Appl. No. 14/611,379, filed Feb. 2, 2015.

Aspect Imaging Ltd., "Method for Providing High Resolution, High Contrast Fused MRI Images", co-pending U.S. Appl. No. 13/877,533, filed May 22, 2014.

(56) References Cited

OTHER PUBLICATIONS

Aspect Imaging Ltd., "Method for Manipulating the MRI's Protocol of Pulse-Sequences", co-pending U.S. Appl. No. 14/070,695, filed Nov. 4, 2013.
Aspect Imaging Ltd., "Foamed Patient Transport Incubator", co-pending U.S. Appl. No. 14/531,289, filed Nov. 3, 2014.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890. filed Oct. 2, 2014.
Aspect Imaging Ltd., "NMR Extractable Probe Cassette Means and Methods Thereof", co-pending U.S. Appl. No. 14/504,907, filed Oct. 2, 2014.
Maramraju, Sri Harsha, et al. Electromagnetic interactions in a shielded PET/MRI system for simultaneous PET/MRI imaging in 9.4 T: evaluation and results, IEEE Transactions on Nuclear Science 59, 5 (2012): pp. 1892-1896.

\* cited by examiner

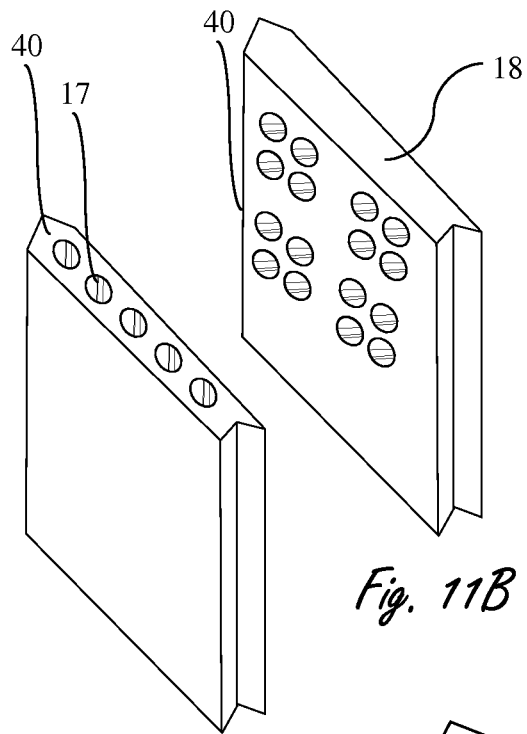
Fig. 11A
Fig. 11B
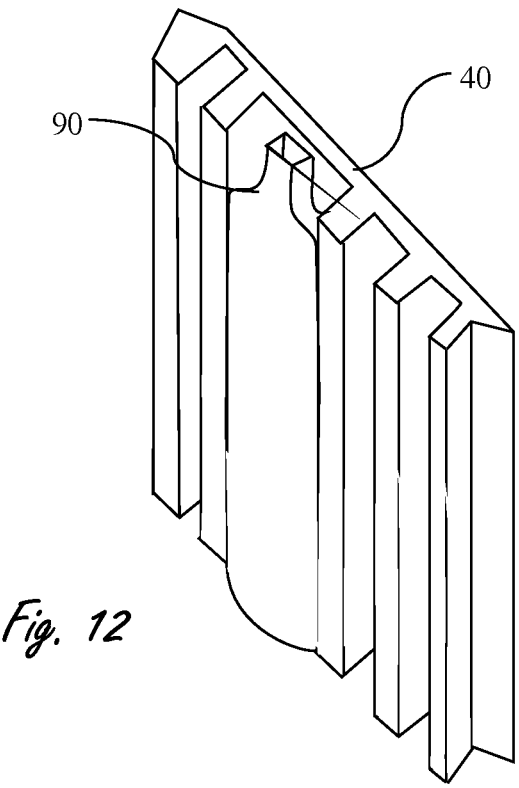
Fig. 12

MRI RF SHIELDING JACKET

FIELD OF THE INVENTION

The present invention generally relates to the field of magnetic resonance imaging systems (MRI), and more particularly, to an MRI jacket, for RF shielding the MRI from the external environment electromagnetic interference during its operation and methods thereof.

BACKGROUND OF THE INVENTION

MRI technology utilizes an interaction between magnetic field and nuclear spins in order to form two-dimensional or three-dimensional images of patients for medical diagnosis and research. To perform a study the patient is positioned within an MRI scanner which forms a strong uniform magnetic field around the area to be imaged. By application of a magnetic field, the hydrogen atoms in the sample (usually originated in water molecules in the body soft tissues) are excited and emit a detectable RF signal using energy from an oscillating magnetic field applied at the appropriate resonant frequency. The distribution of the individual nuclear spins produces an overall magnetization which can be deflected out of the state of equilibrium by application of an electromagnetic pulse of appropriate frequency (RF pulse). In order to realize spatial resolution in the body, switching magnetic field gradients extending along the three main axes are superposed on the uniform magnetic field, leading to a linear spatial dependency of the spin resonance frequency. The contrast between different tissues is determined by the rate at which excited atoms return to the equilibrium state. A set of signal data is then converted to an MR (magnetic resonance image).

Magnetic resonance imaging device (MRD) design is essentially determined by the type and format of the main magnet, i.e. closed, tunnel-type MRI or open MRI.

In general, three main types of magnets are used in MRI systems: resistive, permanent and superconducting. The most commonly used magnets are superconducting electromagnets. These consist of a coil that has been made superconductive by helium liquid cooling, and further maintained cold by a cryocooler, refrigerator, or liquid nitrogen. Superconducting electromagnets produce strong, homogeneous magnetic fields, but are expensive and require regular maintenance.

Additionally, three gradient MRI magnets are used in the MRI machine to help the imaging process. They create a variable field after the other magnets have been activated to generate a stable field, and are turned on and off very quickly to create different pictures or "slices" for spatial distribution of the image, and for enabling analysis of the rate of magnetic decay and recovery between different magnetic pulses, thereby receiving a more thorough and in-depth examination of the patient.

Low field MRI also uses resistive electromagnets, able to create a magnetic field when electricity runs through them. They are cheaper and easier to maintain than superconducting magnets. Resistive electromagnets are far less powerful, use more energy and require a cooling system. Other magnets in use are permanent magnets, of different formats, that are composed of ferromagnetic metallic components. Although they have the advantage of being inexpensive and easy to maintain, they are very heavy and weak in intensity.

Maintaining a uniform and stable magnetic field is a necessity for producing quality imaging. Among the factors affecting this field are temperature, electromagnetic interference, and movement. When referring to small magnetic resonance devices (MRD) the magnet used is usually a permanent magnet. Since a permanent magnet does not produce heat, and being rather small in size the device's heat retention capabilities are low, the MRD is exposed to the environmental temperature. Further, being small in size, thus transportable, requires that the MRD will be able to work in different environmental conditions.

Having a large signal to noise ratio (SNR), the MRD needs to be as un-interrupted as possible during the examination. EMI (electro magnetic interference) generated at an external source such as from electric lines, television and radio signals, elevators, etc., can impede MRI operation and analysis. Even small electrical circuits like a conversion circuit of the DC power source in a computer, can generate electromagnetic interference. EMI can result in serious tampering of the magnetic field uniformity, and impairment of the generated RF signals, therefore resulting in either artifacts or missing information.

Facilities providing MRI services build specially designed rooms that allow MRI procedures to be shielded from these interferences, while preventing leakage of the same interferences to the outside.

This shielding may include passive or active components to achieve magnetic and RF shielding. For example, to achieve RF shielding, the walls, floor and ceiling are built from sheets of conductive metal such as copper, aluminum, etc., including a door that maintains a closed circuit with the walls. Magnetic shielding could be provided by constructing a magnetic shield around the RF shield. A passive solution involves using magnetic shielding material, typically metal or metal alloy. These materials would need to be comprised of a very high permeability material such as "mu-metal". The second option would be an active magnetic cancellation system, that would typically include a magnetometer, controller, amplifier and compensation coils. This solution tends to be costly and requires adjusting and handling.

Obtaining best results from an MRI scan, and thereby increasing the efficiency of the imaging process requires homogeneity of conditions. Homogeneity of the MRI scanning conditions also enables reliable comparison of MRI scans taken at different times from the same individual or sample, allowing for better monitoring of small changes. Other environmental factors like temperature can also affect the uniformity of the magnetic field, by affecting the properties of the magnetic alloys, and by affecting the properties of a scanned sample.

Therefore, there is a need for an RF shielding jacket providing shielding of the MRD from the external environment electromagnetic interference, thereby allowing for homogenized imaging conditions. The present invention further provides an RF shielding jacket combined with passive temperature insulating properties, fitting for an MRD.

SUMMARY OF THE INVENTION

The present invention provides an RF shielding jacket (RFSJ), useful for shielding a magnetic resonance device (MRD) having external dimensions A $[m^2]$, and length $L_0$ [m], from electromagnetic interference (EMI), comprising an envelope sized and shaped to accommodate the MRD, wherein at least a portion of the RFSJ comprises an EMI shield.

It is another object of the current invention to disclose the RFSJ as defined in any of the above, wherein at least a portion of the thermo isolating jacket comprises means for shielding at least a portion of the MRD from a selected from a group consisting of: magnetism, electromagnetic interference, physical damage and any combination thereof.

It is another object of the current invention to disclose the RFSJ as defined in any of the above, wherein the RFSJ comprises a conduit having at least one first aperture to the MRD bore and at least one aperture to the external environment, fitted for the passage of tubing within; further wherein the conduit is configured to attenuate the passage of frequencies selected from a group consisting of: 0 to about 1000 MHz, 0 to about 500 MHz, 0 to about 200 MHz and any combination thereof.

It is another object of the current invention to disclose the RFSJ as defined in any of the above, wherein the conduit is configured to attenuate electromagnetic interference by means selected from a group consisting of: waveguide, RF filter, waveguide filter, attenuating material, and any combination thereof.

It is another object of the current invention to disclose the RFSJ as defined in any of the above, wherein the RFSJ comprises an EMI shield configured to attenuate the passage of frequencies selected from a group consisting of: 0 to about 1000 MHz, 0 to about 500 MHz, 0 to about 200 MHz and any combination thereof.

It is another object of the current invention to disclose the RFSJ as defined in any of the above, configured for an MRD positioned in an atmospheric pressure system and temperature changing environment, having at least one first temperature $T_1$ [° C.] and a Q [kj] amount of heat applied to the same, in which the RFSJ: (a) at least one second temperature $T_2$ [° C.] in the inner portion; (b) a specific mass, m [kg]; and, (c) specific heat capacity, $C_p$ [kj/kg]; wherein the following formula is being held true: $Q = C_p$ m dT; where $dT = T_1 - T_2$, wherein for each applied Q, dT2 is in the range of 0° C.-0.2° C.; where $dT_2 = T_2 + dT$.

It is another object of the current invention to disclose the RFSJ as defined in any of the above, wherein at least a portion of the RFSJ comprises n layers.

It is another object of the current invention to disclose the RFSJ as defined in any of the above, wherein at least 2 of the n layers comprising a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1 - \ldots dHn$, where dT of RFSJ equals $H_1 - Hn$.

It is another object of the current invention to disclose the RFSJ as defined in any of the above, wherein at least one layer comprising shielding selected from a group consisting of: magnetic shielding, RF shielding, physical shielding and any combination thereof.

It is another object of the current invention to disclose the RFSJ as defined in any of the above, wherein at least one layer comprising an electrical isolating material.

It is another object of the current invention to disclose the RFSJ as defined in any of the above, wherein at least one layer closes a conductive circle around the MRD.

It is another object of the current invention to disclose the RFSJ as defined in any of the above, wherein at least a portion of the RFSJ comprising conductive coating, or conductive plating.

It is another object of the current invention to disclose the RFSJ as defined in any of the above, wherein at least a portion of the RFSJ comprising a material selected from a group consisting of: metal, metal containing composite, metal containing foam, metallic plastic composite and any combination thereof.

It is another object of the current invention to disclose the RFSJ as defined in any of the above, wherein at least a portion of the RFSJ is selected from a group consisting of: a metallic plate, a metallic mesh, a metallic web, a perforated metallic plate, a metallic wire interlace and any combination thereof.

It is another object of the current invention to disclose the RFSJ as defined in any of the above, wherein the jacket comprises at least one opening to permit access to the MRD.

It is another object of the current invention to disclose the RFSJ as defined in any of the above, wherein the opening comprises a reversibly connectable door to permit or restrict access to the MRD though the opening.

It is another object of the current invention to disclose the RFSJ as defined in any of the above, wherein at least a portion of RFSJ comprises a material selected from a group consisting of: thermo insulating material, sealing material, foam material, fire retardant materials, at least partially transparent material and any combination thereof.

It is another object of the current invention to disclose the RFSJ as defined in any of the above, wherein the RFSJ is connected to the MRD operating system.

It is another object of the current invention to disclose the RFSJ as defined in any of the above, wherein the RFSJ comprises modular pieces reversibly connectable to form the RFSJ.

It is another object of the current invention to disclose the RFSJ as defined in any of the above, wherein the RFSJ comprises at least one fastener selected from a group consisting of: a connection between the MRI and the RFSJ, structural integrity of the RFSJ, and any combination thereof.

It is another object of the current invention to disclose the RFSJ as defined in any of the above, wherein at least a portion of the RFSJ comprises channels for passage of a substance selected from a group consisting of: gas, liquid, gel, solid particles, and any combination thereof.

It is another object of the current invention to disclose the RFSJ as defined in any of the above, wherein at least a portion comprises an active thermo regulating system.

It is another object of the current invention to disclose the RFSJ as defined in any of the above, wherein the system is configured to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

It is another object of the current invention to disclose the RFSJ as defined in any of the above, wherein at least a portion of the RFSJ comprises a passive thermo-regulating envelope surrounding an active thermo-regulating system.

It is another object of the current invention to disclose the RFSJ as defined in any of the above, wherein the RFSJ comprises at least one sensor selected from a group consisting of: temperature sensors, EMI sensors, magnetic sensors, vibration sensors, connection sensors, and any combination thereof.

It is another object of the current invention to disclose the RFSJ as defined in any of the above, comprising temperature sensors, wherein the sensors are configured to sense the inner volume temperature, the external environment temperature or both.

It is another object of the current invention to disclose the RFSJ as defined in any of the above, wherein the RFSJ is connected to a component selected from a group consisting of: a CPU, an alarm system, at least one indicator, at least one sensor, and any combination thereof.

It is another object of the current invention to disclose the RFSJ as defined in any of the above, wherein at least a portion comprises a user interface.

It is another object of the current invention to disclose the RFSJ as defined in any of the above, wherein at least a portion comprising an RF detecting system; further wherein the system is connected to at least one selected from a group consisting of: an indicator, an alarm system, a user interface and any combination thereof.

It is another object of the current invention to disclose the RFSJ as defined in any of the above, configured for am MRD to be positioned in an atmospheric pressure, temperature changing environment, having at least one first temperature $T_1$ [° C.] and at least one second temperature $T_2$ [° C.], in which the RFSJ: (a) thermal conductivity, k [W/m ° C.]; (b) thickness, s [m]; and, (c) conductive heat transfer, q [W]; wherein the following formula is being held true: q=k A dT/s, where dT equals $T_2-T_1$ and q<<0.01 W.

It is another object of the current invention to disclose the RFSJ as defined in any of the above, comprising at least n layers, wherein at least 2 of the n layers comprising a substantially different conductive heat transfer value q for each layer; where each of the layers has at least one first temperature $H_1$ [° C.] measured on the outer side of the layer, and at least one first temperature $H_2$ [° C.], measured on its inner side towards the MRD, having a $dH_1$-...$dHn$, where dT of the RFSJ equals $H_1-Hn$.

It is another object of the current invention to disclose the RFSJ as defined in any of the above, in an MRD being positioned in an atmospheric pressure and a temperature changing environment having at least one first temperature $T_1$ [° C.] and at least one second temperature $T_2$ [° C.], a RFSJ for the MRD, wherein the RFSJ is characterized by a thermal expansion coefficient substantially different than 0.

It is another object of the current invention to disclose the RFSJ as defined in any of the above, comprising at least n layers, wherein at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1$-...$dHn$, where dT of the RFSJ equals $H_1-Hn$.

It is another object of the current invention to disclose the RFSJ as defined in any of the above, in which: (a) length $L_{0, Jacket}$ [m] fitted by means of size and shape to the $L_{0,MRD}$; and, (b) linear thermal expansion coefficient $\alpha_L$ [° C.$^{-1}$] substantially different than 0; wherein if dT substantially different than 0; the length $L_{0, Jacket}$ will be varied to $L_{1, Jacket}$, such that the formula is being held true for any change in temperature, dT:

$$\alpha_L = \frac{1}{L}\frac{dL}{dT}$$

where dL equals $L_{1, Jacket}-L_{0, Jacket}$ and dT equals $T_2-T_1$.

It is another object of the current invention to disclose the RFSJ as defined in any of the above, in which: (a) volume $V_{0\ Jacket}$ [m]; and (b) volumetric thermal expansion coefficient $\alpha_V$ [° C.$^{-1}$] substantially different than 0; wherein if dT substantially different than 0; the volume $V_{0, Jacket}$ will be varied to $V_{1, Jacket}$, such that the formula is being held true for any change in temperature, dT:

$$\alpha_V = \frac{1}{V}\left(\frac{\partial V}{\partial T}\right)$$

where dV equals $V_{1, Jacket}-V_{0, Jacket}$ and dT equals $T_2-T_1$.

It is another object of the current invention to disclose the RFSJ as defined in any of the above, in which: (a) area $A_{0, Jacket}$ [m$^2$]; and, (b) area thermal expansion coefficient $\alpha_A$ [° C.$^{-1}$] substantially different than 0; wherein if dT substantially different than 0; the length $A_{0, Jacket}$ will be varied to $A_{1, Jacket}$, such that the formula is being held true for any change in temperature, dT:

$$\alpha_A = \frac{1}{A}\frac{dA}{dT}$$

where dA equals $A_{1, Jacket}-A_{0, Jacket}$ and dT equals $T_2-T_1$.

The present invention provides a method for RF shielding an magnetic resonance device (MRD), having external dimensions A [m$^2$], and length $L_0$ [m], from electro magnetic interference (EMI), comprising steps of: (a) obtaining an RFSJ sized and shaped to accommodate the MRD; and (b) operating the same; wherein at least a portion of the RFSJ comprising an EMI shield.

It is another object of the current invention to disclose a method as defined in any of the above, additionally comprising a step of shielding at least a portion of the MRD from a force selected from a group consisting of: magnetism, electromagnetic interference, physical damage and any combination thereof.

It is another object of the current invention to disclose a method as defined in any of the above, additionally comprising a step of selecting the RFSJ comprising a conduit having at least one first aperture to the MRD bore and at least one aperture to the external environment, fitted for the passage of tubing within; further configuring the conduit to attenuate the passage of frequencies selected from a group consisting of: 0 to about 1000 MHz, 0 to about 500 MHz, 0 to about 200 MHz and any combination thereof.

It is another object of the current invention to disclose a method as defined in any of the above, additionally comprising a step of configuring the conduit to attenuate electromagnetic interference by means selected from a group consisting of: waveguide, RF filter, waveguide filter, attenuating material, and any combination thereof.

It is another object of the current invention to disclose a method as defined in any of the above, additionally comprising a step of passing tubing though the conduit.

It is another object of the current invention to disclose a method as defined in any of the above, additionally comprising a step of the RFSJ comprises an EMI shield configured to attenuate the passage of frequencies selected from a group consisting of: 0 to about 1000 MHz, 0 to about 500 MHz, 0 to about 200 MHz and any combination thereof.

It is another object of the current invention to disclose a method as defined in any of the above, additionally comprising a step of configuring the RFSJ for an MRD to be positioned in an atmospheric pressure system and temperature changing environment, having at least one first temperature $T_1$ [° C.] and a Q [kj] amount of heat applied to the same, in which the RFSJ: (a) at least one second temperature $T_2$ [° C.] in the inner portion; (b) a specific mass, m [kg]; and, (c) specific heat capacity, $C_p$ [kj/kg]; wherein the following formula is being held true: $Q=C_p$ m dT; where $dT=T_1-T_2$, wherein for each applied Q, dT2 is in the range of 0° C.-0.2° C.; where $dT_2=T_2+dT$, thereby thermo isolating the MRD.

It is another object of the current invention to disclose a method as defined in any of the above, additionally comprising a step of selecting the RFSJ in which at least a portion of the RFSJ comprises n layers.

It is another object of the current invention to disclose a method as defined in any of the above, additionally comprising a step of selecting the RFSJ in which at least 2 of the n layers comprising a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1$- . . . dHn, where dT of RFSJ equals $H_1$-Hn.

It is another object of the current invention to disclose a method as defined in any of the above, additionally comprising a step of shielding at least one layer with shielding means selected from a group consisting of: magnetic shielding, RF shielding, physical shielding and any combination thereof.

It is another object of the current invention to disclose a method as defined in any of the above, additionally comprising a step of electrically isolating the RFSJ within at least one layer.

It is another object of the current invention to disclose a method as defined in any of the above, additionally comprising a step of closing a conductive circle around the MRD with at least one layer.

It is another object of the current invention to disclose a method as defined in any of the above, additionally comprising a step of selecting at the RFSJ with at least a portion of conductive coating, or conductive plating.

It is another object of the current invention to disclose a method as defined in any of the above, additionally comprising a step of selecting the RFSJ in which at least a portion of having a material selected from a group consisting of: metal, metal containing composite, metal containing foam, metallic plastic composite and any combination thereof.

It is another object of the current invention to disclose a method as defined in any of the above, additionally comprising a step of selecting the RFSJ having at least a portion of selected from a group consisting of: a metallic plate, a metallic mesh, a metallic web, a perforated metallic plate, a metallic wire interlace and any combination thereof.

It is another object of the current invention to disclose a method as defined in any of the above, additionally comprising a step of selecting the RFSJ having at least one opening to permit access to the MRD.

It is another object of the current invention to disclose a method as defined in any of the above, additionally comprising a step of opening or closing the opening with a door.

It is another object of the current invention to disclose a method as defined in any of the above, additionally comprising a step of selecting the RFSJ having at least a portion of a material selected from a group consisting of: thermo insulating material, sealing material, foam material, fire retardant materials, at least partially transparent material and any combination thereof.

It is another object of the current invention to disclose a method as defined in any of the above, additionally comprising a step of connecting the RFSJ to the MRD operating system.

It is another object of the current invention to disclose a method as defined in any of the above, additionally comprising a step of reversibly connecting modular pieces to form the RFSJ.

It is another object of the current invention to disclose a method as defined in any of the above, additionally comprising a step of securing the RFSJ with at least one fastener, selected from a group consisting of: a connection between the MRI and the RFSJ, structural integrity of the RFSJ, and any combination thereof.

It is another object of the current invention to disclose a method as defined in any of the above, additionally comprising a step of selecting the RFSJ having at least a portion of with channels for passage of a substance selected from a group consisting of: gas, liquid, gel, solid particles or any combination thereof.

It is another object of the current invention to disclose a method as defined in any of the above, additionally comprising a step of passing a substance selected from a group consisting of: gas, liquid, gel, solid particles or any combination thereof, in the channels.

It is another object of the current invention to disclose a method as defined in any of the above, additionally comprising a step of operating an active thermo regulating system.

It is another object of the current invention to disclose a method as defined in any of the above, additionally comprising a step of configuring the system to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

It is another object of the current invention to disclose a method as defined in any of the above, additionally comprising a step of selecting the RFSJ having at least a portion of comprising a passive thermo-regulating envelope surrounding an active thermo-regulating system.

It is another object of the current invention to disclose a method as defined in any of the above, additionally comprising a step of selecting the RFSJ having at least one sensor selected from a group consisting of: temperature sensors, EMI sensors, magnetic sensors, vibration sensors, connection sensors, and any combination thereof.

It is another object of the current invention to disclose a method as defined in any of the above, additionally comprising a step of configuring the sensors to sense the inner volume temperature, the external environment temperature or both.

It is another object of the current invention to disclose a method as defined in any of the above, additionally comprising a step of selecting the RFSJ comprising a component selected from a group consisting of: user interface, an RF detection system, A CPU, an alarm system, at least one indicator, and any combination thereof.

It is another object of the current invention to disclose a method as defined in any of the above, additionally comprising a step of connecting and operating the RF detection system to a component selected from a group consisting of: at least one indicator, at least one sensor, user interface, display, an alarm system, and any combination thereof.

It is another object of the current invention to disclose a method as defined in any of the above, additionally comprising a step of connecting the RFSJ to a component selected from a group consisting of: a CPU, an alarm system, at least one indicator, at least one sensor, and any combination thereof.

It is another object of the current invention to disclose a method as defined in any of the above, additionally comprising a step of configuring the RFSJ for an MRD to be positioned in an atmospheric pressure, temperature changing environment, having at least one first temperature $T_1$ [° C.] and at least one second temperature $T_2$ [° C.], in which the RFSJ: (a) thermal conductivity, k [W/m ° C.]; (b) thickness, s [m]; and, (c) conductive heat transfer, q [W]; wherein the following formula is being held true: q=k A dT/s, where dT equals $T_2-T_1$ and q<<0.01 W, thereby thermo isolating the MRD.

It is another object of the current invention to disclose a method as defined in any of the above, additionally comprising a step of selecting the RFSJ having at least n layers, in which at least 2 of the n layers comprising a substantially different conductive heat transfer value q for each layer; in which each of the layers has at least one first temperature $H_1$ [° C.] measured on the outer side of the layer, and at least one first temperature $H_2$ [° C.], measured on its inner side towards the MRD, having a $dH_1-\ldots dH_n$, where dT of the RFSJ equals $H_1-H_n$.

It is another object of the current invention to disclose a method as defined in any of the above, additionally comprising a step of, configuring the RFSJ for an MRD being positioned in an atmospheric pressure and a temperature changing environment having at least one first temperature $T_1$ [° C.] and at least one second temperature $T_2$ [° C.], a RFSJ for the MRD, in which the RFSJ is characterized by a thermal expansion coefficient substantially different than 0.

It is another object of the current invention to disclose a method as defined in any of the above, additionally comprising a step of selecting the RFSJ having at least n layers, in which at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1-\ldots dH_n$, where dT of the RFSJ equals $H_1-H_n$.

It is another object of the current invention to disclose a method as defined in any of the above, additionally comprising a step of selecting the RFSJ in which: (a) length $L_{0, Jacket}$ [m] fitted by means of size and shape to the $L_{0,MRD}$; and (b) linear thermal expansion coefficient $\alpha_L$ [° C.$^{-1}$] substantially different than 0; wherein if dT substantially different than 0; the length $L_{0, Jacket}$ will be varied to $L_{1, Jacket}$, such that the formula is being held true for any change in temperature, dT:

$$\alpha_L = \frac{1}{L}\frac{dL}{dT}$$

where dL equals $L_{1, Jacket}-L_{0,Jacket}$ and dT equals $T_2-T_1$, thereby thermo isolating the MRD.

It is another object of the current invention to disclose a method as defined in any of the above, additionally comprising a step of selecting the RFSJ in which: (a) volume $V_{0\ Jacket}$ [m]; and (b) volumetric thermal expansion coefficient $\alpha_V$ [° C.$^{-1}$] substantially different than 0; wherein if dT substantially different than 0; the volume $V_{0, Jacket}$ will be varied to $V_{1, Jacket}$, such that the formula is being held true for any change in temperature, dT:

$$\alpha_V = \frac{1}{V}\left(\frac{\partial V}{\partial T}\right)$$

where dV equals $V_{1, Jacket}-V_{0,Jacket}$ and dT equals $T_2-T_1$, thereby thermo isolating the MRD.

It is another object of the current invention to disclose a method as defined in any of the above, additionally comprising a step of selecting the RFSJ in which: (a) area $A_{0, Jacket}$ [m$^2$]; and, (b) area thermal expansion coefficient $\alpha_A$ [° C.$^{-1}$] substantially different than 0; wherein if dT substantially different than 0; the length $A_{0, Jacket}$ will be varied to $A_{1, Jacket}$, such that the formula is being held true for any change in temperature, dT:

$$\alpha_A = \frac{1}{A}\frac{dA}{dT}$$

where dA equals $A_{1, Jacket}-A_{0, Jacket}$ and dT equals $T_2-T_1$, thereby thermo isolating the MRD.

The present invention provides a method for manufacturing an RFSJ for shielding a magnetic resonance device (MRD), having external dimensions A [m$^2$], and length $L_0$ [m], from electro magnetic interference (EMI), comprising steps of: (a) sizing and shaping the RFSJ to accommodate the MRD; and (b) forming the RFSJ; in which at least a portion of the RFSJ comprises an EMI shield.

It is another object of the current invention to disclose a method as defined in any of the above, additionally comprising a step of shielding at least a portion of the MRD from a force selected from a group consisting of: magnetism, electromagnetic interference, physical damage and any combination thereof.

It is another object of the current invention to disclose a method as defined in any of the above, additionally comprising a step of constructing the RFSJ comprising a conduit having at least one first aperture to the MRD bore and at least one aperture to the external environment, fitted for the passage of tubing within; further configuring the conduit to attenuate the passage of frequencies selected from a group consisting of: 0 to about 1000 MHz, 0 to about 500 MHz, 0 to about 200 MHz and any combination thereof.

It is another object of the current invention to disclose a method as defined in any of the above, additionally comprising a step of configuring the conduit to attenuate electromagnetic interference by means selected from a group consisting of: waveguide, RF filter, waveguide filter, attenuating material, and any combination thereof.

It is another object of the current invention to disclose a method as defined in any of the above, additionally comprising a step of passing tubing though the conduit.

It is another object of the current invention to disclose a method as defined in any of the above, additionally comprising a step of the RFSJ comprises an EMI shield configured to attenuate the passage of frequencies selected from a group consisting of: 0 to about 1000 MHz, 0 to about 500 MHz, 0 to about 200 MHz and any combination thereof.

It is another object of the current invention to disclose a method as defined in any of the above, additionally comprising a step of configuring the MRD to be positioned in an atmospheric pressure system and temperature changing environment, having at least one first temperature $T_1$ [° C.]

and a Q [kj] amount of heat applied to the same, in which the RFSJ: (a) at least one second temperature $T_2$ [° C.] in the inner portion; (b) a specific mass, m [kg]; and, specific heat capacity, $C_p$ [kj/kg]; wherein the following formula is being held true: $Q=C_p$ m dT; where $dT=T_1-T_2$, wherein for each applied Q, dT2 is in the range of 0° C.-0.2° C.; where $dT_2=T_2+dT$, thereby thermo isolating the MRD.

It is another object of the current invention to disclose a method as defined in any of the above, additionally comprising a step of constructing the RFSJ in which at least a portion of the RFSJ comprises n layers.

It is another object of the current invention to disclose a method as defined in any of the above, additionally comprising a step of constructing the RFSJ having at least 2 of the n layers in which a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1$– . . . dHn, where dT of RFSJ equals $H_1$–Hn.

It is another object of the current invention to disclose a method as defined in any of the above, additionally comprising a step of shielding at least one layer with shielding means selected from a group consisting of: magnetic shielding, RF shielding, physical shielding and any combination thereof.

It is another object of the current invention to disclose a method as defined in any of the above, additionally comprising a step of electrically isolating the RFSJ with at least one layer.

It is another object of the current invention to disclose a method as defined in any of the above, additionally comprising a step of closing a conductive circle around the MRD with at least one layer.

It is another object of the current invention to disclose a method as defined in any of the above, additionally comprising a step of coating or plating at least a portion of the RFSJ with a conductive material.

It is another object of the current invention to disclose a method as defined in any of the above, additionally comprising a step of forming the RFSJ in which at least a portion of having a material selected from a group consisting of: metal, metal containing composite, metal containing foam, metallic plastic composite and any combination thereof.

It is another object of the current invention to disclose a method as defined in any of the above, additionally comprising a step of forming at least a portion of the RFSJ with a selected from a group consisting of: a metallic plate, a metallic mesh, a metallic web, a perforated metallic plate, a metallic wire interlace and any combination thereof.

It is another object of the current invention to disclose a method as defined in any of the above, additionally comprising a step of forming at least one opening in RFSJ permitting access to the MRD.

It is another object of the current invention to disclose a method as defined in any of the above, additionally comprising a step of connecting a maneuverable door to the opening permitting or restricting access to the opening.

It is another object of the current invention to disclose a method as defined in any of the above, additionally comprising a step of forming the RFSJ having at least a portion of a material selected from a group consisting of: thermo insulating material, sealing material, foam material, fire retardant materials, at least partially transparent material and any combination thereof.

It is another object of the current invention to disclose a method as defined in any of the above, additionally comprising a step of connecting the RFSJ to the MRD operating system.

It is another object of the current invention to disclose a method as defined in any of the above, additionally comprising a step of forming modular pieces reversibly connecting to construct the RFSJ.

It is another object of the current invention to disclose a method as defined in any of the above, additionally comprising a step of connecting at least one fastener to secure a selected from a group consisting of: a connection between the MRI and the RFSJ, structural integrity of the RFSJ, and any combination thereof.

It is another object of the current invention to disclose a method as defined in any of the above, additionally comprising a step of forming at least a portion of the RFSJ with channels for passage of a substance selected from a group consisting of: gas, liquid, gel, solid particles or any combination thereof.

It is another object of the current invention to disclose a method as defined in any of the above, additionally comprising a step of passing a substance selected from a group consisting of: gas, liquid, gel, solid particles or any combination thereof, in the channels.

It is another object of the current invention to disclose a method as defined in any of the above, additionally comprising a step of connecting an active thermo regulating system to the RFSJ.

It is another object of the current invention to disclose a method as defined in any of the above, additionally comprising a step of configuring the system to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

It is another object of the current invention to disclose a method as defined in any of the above, additionally comprising a step of constructing the RFSJ having at least a portion of comprising a passive thermo-regulating envelope surrounding an active thermo-regulating system.

It is another object of the current invention to disclose a method as defined in any of the above, additionally comprising a step of connecting at least one sensor to the RSFJ selected from a group consisting of: temperature sensors, EMI sensors, magnetic sensors, vibration sensors, connection sensors, and any combination thereof.

It is another object of the current invention to disclose a method as defined in any of the above, additionally comprising a step of configuring the sensors to sense the inner volume temperature, the external environment temperature or both.

It is another object of the current invention to disclose a method as defined in any of the above, additionally comprising a step of connecting a component selected from a group consisting of: user interface, an RF detection system, A CPU, an alarm system, at least one indicator, and any combination thereof, to the RFSJ.

It is another object of the current invention to disclose a method as defined in any of the above, additionally comprising a step of connecting the RF detection system to a component selected from a group consisting of: at least one indicator, at least one sensor, user interface, display, an alarm system, and any combination thereof.

It is another object of the current invention to disclose a method as defined in any of the above, additionally comprising a step of connecting the RFSJ to a component selected from a group consisting of: a CPU, an alarm system, at least one indicator, at least one sensor, and any combination thereof.

It is another object of the current invention to disclose a method as defined in any of the above, additionally comprising a step of configuring the RFSJ for an MRD to be positioned in an atmospheric pressure, temperature changing environment, having at least one first temperature $T_1$ [° C.] and at least one second temperature $T_2$ [° C.], in which the RFSJ: (a) thermal conductivity, k[W/m ° C.]; (b) thickness, s [m]; and, (c) conductive heat transfer, q [W]; wherein the following formula is being held true: q=k A dT/s, where dT equals $T_2-T_1$ and q<<0.01 W, thereby thermo isolating the RFSJ.

It is another object of the current invention to disclose a method as defined in any of the above, additionally comprising a step of constructing the RFSJ having at least n layers, in which at least 2 of the n layers comprising a substantially different conductive heat transfer value q for each layer; in which each of the layers has at least one first temperature $H_1$ [° C.] measured on the outer side of the layer, and at least one first temperature $H_2$ [° C.], measured on its inner side towards the MRD, having a $dH_1-\ldots dHn$, where dT of the RFSJ equals $H_1-Hn$.

It is another object of the current invention to disclose a method as defined in any of the above, additionally comprising a step of, configuring the RFSJ for an MRD being positioned in an atmospheric pressure and a temperature changing environment having at least one first temperature $T_1$ [° C.] and at least one second temperature $T_2$ [° C.], a RFSJ for the MRD, in which the RFSJ is characterized by a thermal expansion coefficient substantially different than 0.

It is another object of the current invention to disclose a method as defined in any of the above, additionally comprising a step of selecting the RFSJ having at least n layers, in which at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1-\ldots dHn$, where dT of the RFSJ equals $H_1-Hn$.

It is another object of the current invention to disclose a method as defined in any of the above, additionally comprising a step of forming the RFSJ in which: (a) length $L_{0, Jacket}$ [m] fitted by means of size and shape to the $L_{0,MRD}$; and, (b) linear thermal expansion coefficient $\alpha_L$ [° C.$^{-1}$] substantially different than 0; wherein if dT substantially different than 0; the length $L_{0, Jacket}$ will be varied to $L_{1, Jacket}$, such that the formula is being held true for any change in temperature, dT:

$$\alpha_L = \frac{1}{L}\frac{dL}{dT}$$

where dL equals $L_{1, Jacket}-L_{0, Jacket}$ and dT equals $T_2-T_1$, thereby thermo isolating the MRD.

It is another object of the current invention to disclose a method as defined in any of the above, additionally comprising a step of forming the RFSJ in which: (a) volume $V_{0\ Jacket}$ [m]; and (b) volumetric thermal expansion coefficient $\alpha_V$ [° C.$^{-1}$] substantially different than 0; wherein if dT substantially different than 0; the volume $V_{0, Jacket}$ will be varied to $V_{1, Jacket}$, such that the formula is being held true for any change in temperature, dT:

$$\alpha_V = \frac{1}{V}\left(\frac{\partial V}{\partial T}\right)$$

where dV equals $V_{1, Jacket}-V_{0,Jacket}$ and dT equals $T_2-T_1$, thereby thermo isolating the MRD.

It is another object of the current invention to disclose a method as defined in any of the above, additionally comprising a step of forming the RFSJ in which: (a) area $A_{0, Jacket}$ [m$^2$]; and, (b) area thermal expansion coefficient $\alpha_A$ [° C.$^{-1}$] substantially different than 0; wherein if dT substantially different than 0; the length $A_{0, Jacket}$ will be varied to $A_{1, Jacket}$, such that the formula is being held true for any change in temperature, dT:

$$\alpha_A = \frac{1}{A}\frac{dA}{dT}$$

where dA equals $A_{1, Jacket}-A_{0, Jacket}$ and dT equals $T_2-T_1$, thereby thermo isolating the MRD.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

FIG. 11A is a schematic illustration of an embodiment of top perforated parts of the MRD RFSJ;

FIG. 11B is a schematic illustration of an embodiment of side perforated parts of the MRD RFSJ;

FIG. 12 is a schematic illustration of an embodiment of corrugated parts of the MRD RFSJ;

DETAILED DESCRIPTION OF THE PREFERRED EMBODIMENTS

Figure 1A:
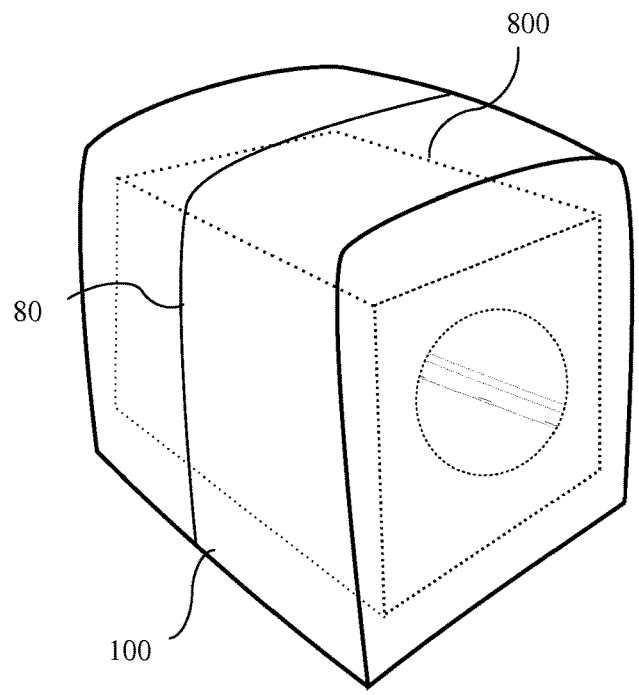
FIG. 1A is a schematic illustration of an MRD RFSJ.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide an RF shielding jacket fitted to accommodate an MRD that shields of the MRD from the external environment electromagnetic interference, thereby stabling conditions for the operation of the MRD. The present invention further provides RF shielding in combination with passive thermo isolation of an MRD. The RF shielding jacket of the present invention will enable quality imaging consistent with changing environmental conditions, thereby increasing the efficiency of MRD examinations.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device.

The term "external environment" refers hereinafter to the external space outside of the MRD.

The term "about" refers hereinafter to 20% more or less than the defied value.

The term "signal-to-noise ratio" refers hereinafter to a measure used to compare the level of a desired signal to the level of background noise. A ratio greater than 1:1 indicates more signal than noise. In imaging, the signal to noise ratio indicates the sensitivity of the imaging, resulting in image quality.

The term "patient" interchangeably refers herein after to a term selected from a group of: neonate, baby, infant, toddler, child, adolescent, adult, elderly, etc.; further this term refers to a whole patient or a portion thereof; further this term refers to person, animal or sample.

The term "connected" in reference to the MRD, RFSJ, parts and modules, interchangeably refers hereinafter to any contact, relation, association, integration, interconnection, joining, inserting, sewing, welding, interweaving, placing, nesting, layering, akin, linkage, unity, alliance, bracketed, combination, coupling, banding, bonding, affiliation, fitting, pairing, attachment, hooking, hinging, welding, adhering, fusion, fixing, tying, sewing, embedding, weaving, etc., of the RFSJ parts to each other and to a third party. When in an embodiment the RFSJ comprises at least two connected parts, the parts can be separated one from the other in a manner selected from a group consisting of: sliding, uncovering, dividing, rupturing, cleaving, disjoining, splitting, bending, screwing, swinging, opening, separating, dismounting, embedding, interweaving, uncoupling, implanting, detaching, breaking, hatching, pulling, peeling, untying, pushing, turning, levering, releasing, unlinking, pressing, moving, snapping, unscrewing, fitting, placing, adhering, disconnecting and any combination thereof; and contrariwise connected to each other in a manner selected from a group consisting of: sliding, covering, joining, bending, screwing, swinging, pairing, mounting, embedding, interweaving, coupling, implanting, attaching, pulling, tying, pushing, turning, levering, linking, pressing, moving, snapping, fitting, placing, adhering, connecting, interconnecting, bonding and any combination thereof.

The term "covering" interchangeably refers hereinafter to fully or partly sealing, connecting, engulfing, surrounding, sheltering, roofing, isolating, insulating, constructing, veiling, shielding, housing, sun-shading, cloaking, enveloping, encapsulating, tracing, layering, placing, wrapping, shelling, casing, screening, boxing, masking, dressing, embracing, tenting, canopy placing, umbrella placing, embedding an additional material to the object/inner volume envelope, concealing, defending, protecting, segregating from, separating from, etc., a defined volume.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non transparent materials for means of strength and/or conductivity such as metallic wires.

The term "foam" interchangeably refers hereinafter to materials such as Styrofoam® commercially available from The Dow Chemical Company, polystyrene foam, high-impact polystyrene, polybutadiene, polyurethane foam, polyvinyl chloride foam, polyimide foam, silicone foam, polymethacrylimide foam, polypropylene foam, polyethylene foam, syntactic foam, rubber, polybutadiene rubber, carbon, cellulose, starch, graphite, acrylonitrile, maleic anhydride, divinylbenzene, polyisocyanurate, cementitious foam, ceramics, glass, silica, etc. Further this foam is open cell, closed cell foam, aerogels (biofoam) and can contain micro-balloons of an additional material such as glass, carbon, epoxy, etc.

The term "rubber" interchangeably refers hereinafter to materials such as natural rubber, isoprene rubber, polyisoprene, latex, butadiene rubber, styrene butadiene, nitrile rubber, butyl rubber, ethylene propylene rubber, chloroprene rubber, hypalon rubber, fluroelastomer rubber, polyacrylic rubber, urethane rubber, silicon rubber, epichlorohydrin rubber, etc.

The term "thermo insulating material" interchangeably refers hereinafter to any materials that are able to thermo-isolate an object or an inner volume from the environment. Thermo insulating materials usually have low heat conductivity values, and/or high heat capacity. The form of this material is selected from a group consisting of: solid, liquid e.g. deionized water, supplemented or not with antifreeze, foam, sheets, granulate, sand, cloth, weave, rope, knit, fiber, particles, cast, spray, aerogel, rods, plates, membrane, bricks, rubber, foil or any combination thereof. Further, the form of this material is such as: a type of foam as defined above, a type of rubber as defined above, ceramic fiber, ceramics, aluminium-magnesium silicate, yarn, knitted ropes, fiber glass, mineral wool, perlite, cellulose, rock wool, basalt, slag wool, cardboard, paper, aerogel products such as Pyrogel® XT, available commercially from Therma XX Jackets, LLC., silica aerogel, aerographene, carbon aerogels, resorcinol formaldehyde aerogel, alumina aerogels, nickel alumina aerogel, SEAgel (Safe Emulsion Agar gel), chalcogel, calcium silicate, phenolic compounds, thinsulate, urea-formaldehyde, icynene, concrete, wood, natural fibers such as hemp, sheep's wool, cotton, straw, cotton batts, cork, brick, asbestos.

The term "sealing material" interchangeably refers hereinafter to materials able to fasten or close tightly by an object or a defined volume thereby not permitting the passage of liquid, solid, or gas from the external environment to the defined volume and contrariwise. This is achieved by covering (as defined above) by elements such as wrap, cloth, fiber, sheet, plate, tent, weave, spray, paint, paste, brick, etc. Further, this element is of a material such water proof, water resistant, vacuum resistant, gas tight, drift resistant, etc.

The term "fire retardant materials" interchangeably refers hereinafter to materials such as tetrabromobisphenol-a, decabromdiphenyl ether, hexabromcyclododecane, chloroparaffins, dedecachloro-pentacyclooctadecadiene, diphenyl phosphate, triaryl phosphates, metal phosphinates, 9,10-dihydro-9-oxa-10-phosphaphenanthrene-10-oxide, trischloropropyl phosphate, ammonium polyphosphate, red phosphorous, melamine, melamine cyanurate, melamine polyphosphate, melamine polyzinc, melamine polyaluminum, phosphates, melamine-based HALS (Hindered Amine Light Stabilizer), intumescent flame retardant systems, metal hydroxides, zinc compounds antimony trioxide, expandable graphite, organo-layered silicates, natural oil polyols etc.

The term "passive thermo-regulating" interchangeably refers hereinafter to any mean that reduces the delta of temperature change of an inner volume or object in reference to the temperature of the external environment, being the object of action rather than causing action (opposed to active). This is achieved by means such as partly or fully covering, with an object or material such as thermo-insulating material as defined above, materials with thermal mass properties, utilizing thermal expansion properties, sealing material etc.

The term "Thermal mass" interchangeably refers hereinafter to a quality of an object that describes how the mass of the object provides "inertia" against temperature fluctuations. For example, when outside temperatures are fluctuating throughout the day, a large thermal mass within the insulated portion of a house can serve to "flatten out" the daily temperature fluctuations, since the thermal mass will absorb thermal energy when the surroundings are higher in temperature than the mass, and give thermal energy back when the surroundings are cooler, without reaching thermal equilibrium. As depicted in Wikipedia, scientifically, thermal mass is equivalent to thermal capacitance or heat capacity, the ability of a body to store thermal energy. It is typically referred to by the symbol $C_{th}$ and measured in units of J/° C. or J/K (which are equivalent). Thermal mass may also be used for bodies of water, machines or machine parts, living things, or any other structure or body in engineering or biology. In those contexts, the term "heat capacity" is typically used instead.

The equation relating thermal energy to thermal mass is:

$$Q = C_{th} \Delta T$$

where Q is the thermal energy transferred, $C_{th}$ is the thermal mass of the body, and $\Delta T$ is the change in temperature For a body of uniform composition, $C_{th}$ can be approximated by $$C_{th} = m c_p$$

where m is the mass of the body and $c_p$ is the isobaric specific heat capacity of the material averaged over temperature range in question.

The term "Thermal expansion" interchangeably refers hereinafter to a tendency of matter to change in length/area/volume in response to a change in temperature. When a substance is heated, its particles begin moving more and thus usually maintain a greater average separation. Materials which contract with increasing temperature are unusual; this effect is limited in size, and only occurs within limited temperature ranges. The degree of expansion divided by the change in temperature is called the material's coefficient of thermal expansion and generally varies with temperature.

The coefficient of thermal expansion describes how the size of an object changes with a change in temperature. Specifically, it measures the fractional change in size per degree change in temperature at a constant pressure. Several types of coefficients have been developed: volumetric, area, and linear. In the general case of a gas, liquid, or solid, the volumetric coefficient of thermal expansion is given by $$\alpha_V = \frac{1}{V}\left(\frac{\partial V}{\partial T}\right)_p$$

The subscript p indicates that the pressure is held constant during the expansion (atmospheric pressure). For a solid, we can ignore the effects of pressure on the material, and the volumetric thermal expansion coefficient can be written:

$$\alpha_V = \frac{1}{V}\frac{dV}{dT}$$

where V is the volume of the material, and dV/dT is the rate of change of that volume with temperature.

If we already know the expansion coefficient, then we can calculate the change in volume $$\frac{\Delta V}{V} = \alpha_V \Delta T$$

Other forms of thermal expansion in solids could be a linear or an area expansion.

Linear expansion is described as change in length measurements of an object ("linear dimension" as opposed to, e.g., volumetric dimension) due to thermal expansion is related to temperature change by a "linear expansion coefficient". It is the fractional change in length per degree of temperature change. Assuming negligible effect of pressure, we may write:

$$\alpha_L = \frac{1}{L}\frac{dL}{dT}$$

where L is a particular length measurement and dL/dT is the rate of change of that linear dimension per unit change in temperature.

The change in the linear dimension can be estimated to be:

$$\frac{\Delta L}{L} = \alpha_L \Delta T$$

The area thermal expansion coefficient relates the change in a material's area dimensions to a change in temperature. It is the fractional change in area per degree of temperature change. Ignoring pressure, we may write:

$$\alpha_A = \frac{1}{A}\frac{dA}{dT}$$

where A is some area of interest on the object, and dA/dT is the rate of change of that area per unit change in temperature.

The change in the linear dimension can be estimated as:

$$\frac{\Delta A}{A} = \alpha_A \Delta T$$

For exactly isotropic materials, and for small expansions, the volumetric thermal expansion coefficient is three times the linear coefficient:

$$\alpha_V = 3\alpha_L$$

The term "Specific heat capacity" interchangeably refers hereinafter to a measurable physical quantity of heat energy required to change a unit mass of a substance by one degree in temperature. The heat supplied to a unit mass can be expressed as:

$$dQ = mcdt$$

Where dQ=heat supplied (kJ, Btu); m=unit mass (kg, lb); c=specific heat capacity (kJ/kg °C., kJ/kg °K, Btu/lb °F.); dt=temperature change (K, °C., °F.); Expressing Specific Heat using: c=dQ/m dt.

The term "active thermo-regulating system" interchangeably refers hereinafter to a system that controls the temperature either by heating or by cooling or both, providing climate control. More specifically, the term relates to an air conditioned system, venting system, liquid (e.g. water) cooling system, a refrigerator system such as compressor refrigerator, absorption refrigerators, solar refrigerators, magnetic refrigerators, acoustic refrigerators, a vapor compression cycle mechanism), infrared heater, a water/oil-heated radiator, a coiled heater, an open coil air heater, a round open coil air heater, a convection heater, straight or formed tubular heaters, a quartz tube air heater, a capacitor-type heater, a Pelletier module, etc.

The term "venting module" interchangeably refers hereinafter to a module that circulates air and distributes it either evenly or in a defined direction. More specifically the term relates to a fan, a jet, a blower, a compressor, a pump, etc. In an embodiment the RFSJ comprises a venting module, assisting in active thermo regulating the MRD.

The term "electromagnetic interference" interchangeably refers hereinafter to electromagnetic interference (EMI), and radio-frequency interference (RFI), derived from electromagnetic radiation, electromagnetic induction, magnetism, electrostatic fields etc., that affect any electrical circuit, or imaging device such as MRD, NMR, ESR, NQR, CT, US, etc. This interference is derived from any source natural or artificial such as earth magnetic field, atmospheric noise, moving masses of metal, electrical lines, subways, cellular communication equipment, electrical devices, TV and radio stations, elevators, etc. This interference can interrupt, obstruct, degrade, limit, result in false data, etc., the effective performance of the circuit or device.

The term "electromagnetic shielding" refers hereinafter to a practice, device, or material aimed at reducing the electromagnetic field in a space by blocking the field with barriers made of conductive or magnetic materials. A device or object aimed at attenuating, blocking, reducing, shielding from or transforming the passage of EMI is referred to herein as an "EMI shield". The shielding reduces the affect of electromagnetic interference (EMI) such as radio waves, electromagnetic fields and electrostatic fields. Shielding is typically applied to isolate devices from the external environment and to cables in order to isolate wires from the environment through which the cable runs. Means for EMI shielding can operate by reflection, absorption, or by carrying the electromagnetic radiation to ground. The fundamental aim is to establish a Faraday cage to provide an EMI shield. This shielding is achieved by means such as a metallic coating of an object to be shielded, forming a Faraday cage. This coating could be perforated as long as the depth and diameter of the perforations are designed as not to allow the passage of EMI. Adequate grounding is also provided, to improve shielding. This is achieved by materials such as metals, materials integrated with metals, such as foam integrated with metals, etc. The main methods of establishing a Faraday cage and EMI shielding are metallic casing, impregnation of a polymer (conductive compounds), conductive coating (metal painting, metal plating, electroless plating, vacuum metallizing). Using conductive plastics is another mean of achieving EM shielding. They work by including either conductive metals or conductive metallized fibers into the bulk of the material. The fibers have a high aspect ratio (length to thickness) and form a continuous conducting network inside the bulk plastic to provide the EMI shielding. These fibers are added in conjunction with a thermoplastic matrix and the overall compound can also include flame retardants or other additives. When having perforations configured to attenuate the EMI, the ratio between the length (l) and the width (w) of the perforations or opening is greater than a predefined value n, further the numerical value of n is selected from a group consisting of: $2.5<n<6$, $4<n<6$, $4<n<9$ and any combination thereof. Other means of EMI shielding are by using waveguides, RF filters, waveguide filter, capacitators, attenuating material, attenuating architecture of the shield like for example leading the EMI to a location from which it cannot pass, an RF screen, active RF shielding means and etc. any conductive material can be used for such as any metallo-containing material, conductive rubber, conductive felt, conductive plastic, conductive foam, metal, composite containing metal or conductive compound materials. Also usable are metallic (with copper e.g.) coating or plating, wire mess, or screens of conductive material. This shielding may include passive or active components to achieve magnetic and RF shielding. For example, to achieve RF shielding, the walls, floor and ceiling are built from sheets of conductive metal such as copper, aluminum, etc., including a door that maintains a closed circuit with the walls.

The term "magnetic shielding" refers hereinafter to a practice or device aimed at reducing the magnetic field in a space. Means for magnetic shielding are for example by applying high permeability and low coercivity metal alloys such as "mu-metal" that draw the magnetic shield and contain it such as nickel containing alloys, or an active magnetic shielding system that produces both homogeneous and spatial gradient magnetic fields. The system is composed of anisotropic magneto resistive sensors, a digital signal processor controller and two different coil systems. Magnetic shielding could be provided by constructing a magnetic shield around the RF shield. A passive solution involves using magnetic shielding material, typically metal or metal alloy.

The term "RF shielding" refers hereinafter to electromagnetic shielding that blocks radio frequency electromagnetic radiation.

The term "waveguide" interchangeably refers hereinafter to a structure that guides waves, such as electromagnetic waves or sound waves. The geometry of a waveguide reflects its function. Wave guides are constructed in different forms such as a hollow shape, solid rod, wire, etc. They are typically constructed from either conductive or dielectric materials. The frequency of the transmitted wave also dictates the shape of a waveguide. As depicted in Wikipedia, electromagnetic wave propagation along the axis of the waveguide is described by the wave equation, which is derived from Maxwell's equations, and where the wavelength depends upon the structure of the waveguide, and the material within it (air, plastic, vacuum, etc.), as well as on the frequency of the wave.

The term "waveguide cutoff" interchangeably refers hereinafter to a boundary in a system's frequency response at which energy flowing through the system begins to be reduced, attenuated or reflected rather than passing through. This property is a derivate of the size and shape of the waveguide. Therefore waveguides are designed to attenuate a specific range of frequencies having a defined amplitude, and wave length that are not able physically to propagate within a specific geometry.

The term "cutoff frequency", (fc) interchangeably refers hereinafter to the frequency beyond which the waveguide no longer effectively contains EMI. Thus, any exciting frequency lower than the cutoff frequency will be attenuated, rather than propagated through the waveguide.

The term "RF filter" interchangeably refers hereinafter to components designed to filter signals in the MHz to GHz frequency ranges. This frequency range is the range used by most broadcast radio, television, wireless communication. These components exert some kind of filtering on the signals transmitted or received. The filters could be active or passive such as waffle-iron filter, mechanical RF filter, etc. RF filters are usually placed when there is need to pass an electrical wire in or out of an MRD enclosure to ensure that the EMI does not couple on the conductive wiring. These filters could be of passive components such as a combination of inductors and capacitors.

The term "RF detection system" interchangeably refers hereinafter to a system designed to detect and alert of the presence of predefined RF waves. This system will typically include a sensor such as an antenna, and an indicator.

The term "Eddy currents" interchangeably refers hereinafter to electric currents induced within conductors by a changing magnetic field in the conductor. As depicted in Wikipedia, These circulating eddies of current have inductance and thus induce magnetic fields. These fields can cause repulsion, attraction, propulsion, drag, and heating effects. The stronger the applied magnetic field, the greater the electrical conductivity of the conductor, and the faster the field changes, the greater the currents that are developed and the greater the fields produced. One important aspect in magnetic resonance imaging is effective shielding using RF (radio frequency) shields (or RF screens). The RF-screen must be well conducting to act as a shield. However, a favorable highly conducting RF-screen which effectively blocks the RF signals, acts at the same time as a medium in which Eddy currents can be induced due to the switching magnetic field gradients in the kHz-range. These Eddy currents cause substantial heat dissipation in the RF-screen. Thus, another requirement of an RF screen the RF-screen is able to effectively suppress the development of Eddy currents. However, good RF-screening requires highly conductive materials, whereas highly conductive materials lead to the development of unwanted Eddy currents. In order to solve this conflict typically silted RF-screens are used, wherein the slits of the RF-screen are bridged by capacitors to 'close' them for RF. These capacitors can either be discreet components or they may also be distributed capacitors.

The term "physical damage shielding means" interchangeably refers hereinafter to any mean that creates at a partial protective layer (actual or virtual) over an object. This is achieved by means such as a foam coating, layering of absorptive material, projections from the object protecting against damage from large items, a wire mess or at least a partial cage from strong materials, protection against electrocution, water isolating coverage, fire resistant properties, etc.

The term "CPU-central processing unit" interchangeably refers hereinafter to the hardware within a computer that carries out the instructions of a computer program by performing the basic arithmetical, logical, and input/output operations of the system.

The term "sensing equipment" interchangeably refers hereinafter to any device that receives a signal or stimulus (heat, pressure, light, motion, sound, humidity etc.) and The term "user interface" interchangeably refers hereinafter to at least one defined area in which the user interacts with the RFSJ. This area harbors: passage for medical equipment, display, CPU, alarm system, monitoring system, power supply, open mechanism, close mechanism, indicators, etc. The user interface is designed for the handler, user or both.

The term "module" interchangeably refers hereinafter to a structurally independent part, able to be connected and detached from the RFSJ. This module is connected itself or by another element in its contour, embedded, integrated, placed, interconnected, etc. to the RFSJ.

The term "visual indicators" interchangeably refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "audible indicators" interchangeably refers hereinafter to a representation of sound, typically as an electrical voltage. Audible indicators have frequencies in the audio frequency range of roughly 20 to 20,000 Hz (the limits of human hearing). Audible indicators are either synthesized directly, or originate at a transducer such as a microphone, musical instrument pickup, phonograph cartridge, or tape head.

The term "sensible indicators" interchangeably refers hereinafter to a physical movement of at least a portion of the user interface, which is noticeable to the user (shaking, vibrating, quivering, etc.).

The term "predetermined values" interchangeably refers hereinafter to physical values of such as temperature, humidity, gas flow, gas concentration, sound pressure levels, vibrations, drift, electricity, radio frequency; system values such data transfer, opened or closed state of RFSJ, structural integrity of RFSJ, structural integrity of interconnected parts, general function of MRD, general function of RFSJ, all of which have a desired value or value range that is predefined to fit a specific action.

The term "fastener" interchangeably refers hereinafter to a mechanism or device that maintains the structural integrity a selected from a group consisting of: the RFSJ itself, its connected parts and modules, the RFSJ door in a closed position, the RFSJ together with the MRD, the RFSJ together with the MRD further connected to a third party, and any combination thereof. Further, this mechanism is such as a belt, strip, fastener, draw latch, latch, lock, bolt, grip, bar, bond, clamp, clasp, connection, fixture, link, hook, hasp, buckle, harness, clip, snap, pin, peg, grapnel, screw, fitting, slide, track, joint, interweave, coupler, chain, implant, staple, cover, layer, connector, inter-connector, insert, hold, ring, etc.

The term "power supply" interchangeably refers hereinafter to a source of power such as electrical power generated from internally supplied DC, externally supplied AC or DC, or both, other energy sources that may be used directly such as solar energy.

The term "door" interchangeably refers hereinafter to a door, screen, panel, cover, plate, hatch, portal, leaf, slip, gate, plank, strip, board, flap, overlay, sheet, membrane, fence, film, pane, façade, barrier, blockade, partition, entry, etc.

The term "maneuverable connection" interchangeably refers hereinafter to any connection that enables movement of one part relative to the other. Further this could be any reversible connection. This can be achieved by an element such as a hinge, fold, slide, rail, magnetic connection, pivot point, joint, bearing, link, pin, hook, elbow, knee, spring, ball and socket, juncture, axis, shaft, telescopic arms, turning point, knot, annexation, coupling, plug-in, crossing, swivel, lock and key, up and over mechanism, etc.

The term "hinge" interchangeably refers hereinafter to any maneuverable connection for rotational motion between the current invention parts, portions and modules, such as a flexible mechanism or material, joint, hook, thread, axis, juncture, fold, bend, elbow, knee, corner, fork, axis, pole, ball and socket, condyloid joint, mechanical device, fold hinge, joint, bearing, barrel hinge, pivot hinges, butt/mortise hinges, case hinges, continuous hinges, piano hinges, concealed hinges, cup hinge, euro hinge, butterfly hinges, parliament hinges, dovetail hinges, flag hinges, flag hinge, strap hinges, H hinges, HL hinges, counter-flap hinge, flush hinge, coach hinge, rising butt hinge, double action spring hinge, tee hinge, friction hinge, security hinge, cranked hinge, lift-off hinge, self-closing hinge, butt hinge, butler tray hinge, card table hinge, drop leaf table hinge, floating hinge, living hinge, and any combination thereof.

The term "pivot pin" interchangeably refers hereinafter to any maneuverable connection for rotational motion between the current invention parts, portions and modules at least partially around a pivot point.

The term "sliding mechanism", interchangeably refers hereinafter to a mechanism in with a body is movable in a sliding motion along a track. A portion of the movable body is mounted on, suspended from, inserted to, threaded to, interweaved with, integrated to, fitted to, following, etc. a track. In reference to a physical track, the connection of the moveable portion to the track is directly by geometrical shape fit of on part with the other and/or via a third element such as wheels, rack wheels, ball bearings, rollers, rolling discs, lubricant, location guide, belts, pulleys etc. In reference to a virtual motion track, the movable portion is connected to a sliding motion providing mechanism such as telescopic arms, folding arms, arms, angled arms, etc. connected at a pivotal point, allowing for sliding movement along a predefined virtual path. In addition this sliding mechanism may enable straight sliding, curved sliding, folding slide, sliding around a corner, rolling door sliding, etc.

The term "medical equipment tubing" interchangeably refers hereinafter to all tubes, cables, connectors, wires, liquid carriers, gas carriers, electrical wires, monitoring cables, viewing cables, data cables, etc., that is used in connection to life support equipment, medical equipment or physical environment maintenance or monitoring.

The value of n interchangeably refers to any integer.

According to one embodiment of the present invention an RF shielding jacket (RFSJ), useful for shielding a magnetic resonance device (MRD) having external dimensions A $[m^2]$, and length $L_0$ [m], from electromagnetic interference (EMI), comprising an envelope sized and shaped to accommodate the MRD, wherein at least a portion of the RFSJ comprises an EMI shield.

According to another embodiment of the invention, an RFSJ as defined above is disclosed an RF shielding jacket (RFSJ), useful for shielding a magnetic resonance device (MRD) having external dimensions A $[m^2]$, and length $L_0$ [m], from electro magnetic interference (EMI), comprising an envelope sized and shaped to contain at least a portion of the MRD, wherein at least a portion of the RFSJ comprises shielding means against electromagnetic radiation from the external environment to the MRD and contrariwise.

According to another embodiment of the invention, an RFSJ as defined above is disclosed, wherein at least a portion of the thermo isolating jacket comprises means for shielding at least a portion of the MRD from a force selected from a group consisting of: magnetism, electromagnetic interference, physical damage and any combination thereof.

According to another embodiment of the invention, an RFSJ as defined above is disclosed, wherein the RFSJ comprises a conduit having at least one first aperture to the MRD bore and at least one aperture to the external environment, fitted for the passage of tubing within; further wherein the conduit is configured to attenuate the passage of frequencies selected from a group consisting of: 0 to about 1000 MHz, 0 to about 500 MHz, 0 to about 200 MHz and any combination thereof.

According to another embodiment of the invention, a RFSJ as defined above is disclosed, wherein the RFSJ comprises a conduit with RF attenuation properties. These attenuation properties are reached by constructing the conduit with means selected from a group consisting of: waveguide, RF filter, waveguide filter, attenuating material, and any combination thereof. When constructed as a waveguide, the EMI is below the waveguide cutoff. Further an RF filter can be installed defined to block RF of defined range. RF filters would provide protection to electrical power, data cables, medical equipment tubing etc.

According to another embodiment of the invention, an RFSJ as defined above is disclosed, wherein the conduit is configured to attenuate electro magnetic interference.

According to another embodiment of the invention, an RFSJ as defined above is disclosed, wherein the conduit is affixed to the RFSJ at a location of at least a portion of the perimeter between the closure assembly and the MRD.

According to another embodiment of the invention, an RFSJ as defined above is disclosed, wherein at least a portion of the RFSJ is perforated, further wherein the perforations are of a length and diameter configured as a waveguide with a cutoff frequency selected from a group consisting of: 0 to about 1000 MHz, 0 to about 500 MHz, 0 to about 200 MHz or the like as needed to meet the frequency of a specific MRD, and the frequency of EMI generated externally. These holes in the closure assembly are made to allow ventilation and light penetration in an otherwise closed space. Another reason for perforating the RFSJ is to reduce the overall weight of the RFSJ.

According to another embodiment of the invention, a RFSJ as defined above is disclosed, wherein at least a portion of the RFSJ acts as a passive electromagnetic shield. In order to create an effective non-active magnetic shielding at least a portion of the closure assembly is constructed from magnetic alloys with high permeability and low coercivity such as Permalloy, and different types of Mu-metal. These are constructed from elements such as metal sheet, metal casting, metal screen, metal containing foam, metallic ink and any combination thereof. Further taking into consideration the possibility of creating Eddy currents, the RFSJ jacket can be constructed with thin plates of conductive material, with metal coating or combined with capacitors to help dissipate these currents.

According to another embodiment of the invention, an RFSJ as defined above is disclosed, wherein the RFSJ further comprises an emergency release mechanism.

According to another embodiment of the invention, an RFSJ as defined above is disclosed, wherein the RFSJ comprises EMI shielding configured to attenuate the passage of frequencies selected from a group consisting of: 0 to about 1000 MHz, 0 to about 500 MHz, 0 to about 200 MHz and any combination thereof.

According to another embodiment of the invention, an RFSJ as defined above is disclosed, in an atmospheric pressure system, temperature changing environment, having (i) at least one first temperature $T_1$ [° C.] and (ii) a Q [kj] amount of heat applied to the same, the RFSJ for an MRD, characterizes by: (a) at least one second temperature $T_2$ [° C.] in the inner portion; (b) a specific mass, m [kg]; and (c) specific heat capacity, $C_p$ [kj/kg]; wherein the following formula is being held true: $Q=C_p$ m dT; where $dT=T_1-T_2$, wherein for each applied Q, dT2 is in the range of 0° C.-0.2° C.; where $dT_2=T_2+dT$.

According to another embodiment of the invention, an RFSJ as defined above is disclosed, wherein at least a portion of the RFSJ comprises n layers.

According to another embodiment of the invention, an RFSJ as defined above is disclosed, wherein at least 2 of the n layers comprising a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1$- ... dHn, where dT of RFSJ equals $H_1$-Hn.

According to another embodiment of the invention, an RFSJ as defined above is disclosed, configured for an MRD positioned in an atmospheric pressure system and temperature changing environment, having at least one first temperature $T_1$ [° C.] and a Q [kj] amount of heat applied to the same, in which the RFSJ: (a) at least one second temperature $T_2$ [° C.] in the inner portion; (b) a specific mass, m [kg]; and, (c) specific heat capacity, $C_p$ [kj/kg]; wherein the following formula is being held true: $Q=C_p$ m dT; where $dT=T_1-T_2$, wherein for each applied Q, dT2 is in the range of 0° C.-0.2° C.; where $dT_2=T_2+dT$.

According to another embodiment of the invention, an RFSJ as defined above is disclosed, wherein at least one layer comprises shielding selected from a group consisting of: magnetic shielding, RF shielding, physical shielding and any combination thereof.

According to another embodiment of the invention, an RFSJ as defined above is disclosed, wherein at least one layer comprising an electrical isolating material.

According to another embodiment of the invention, an RFSJ as defined above is disclosed, wherein the at least a portion of the RFSJ, the outer structure of the MRD or any combination thereof, form a conductive circuit. This could be formed with the RFSJ alone, with the existing MRD, with another element surrounding the MRD or any combination thereof. This arrangement will serves as an electromagnetic shield. Further wherein at least a portion of the RFSJ, and the surrounding elements, are typically made of metal such as copper, galvanized steel, aluminum etc detachment of at least one hinged connected member.

According to another embodiment of the invention, an RFSJ as defined above is disclosed, wherein at least a portion of the RFSJ comprises conductive coating, or conductive plating.

According to another embodiment of the invention, an RFSJ as defined above is disclosed, wherein at least a portion of the RFSJ comprising a material selected from a group consisting of: metal, metal containing composite, metal containing foam, metallic plastic composite and any combination thereof.

According to another embodiment of the invention, an RFSJ as defined above is disclosed, wherein at least a portion of the RFSJ is selected from a group consisting of: a metallic plate, a metallic mesh, a metallic web, a perforated metallic plate, a metallic wire interlace and any combination thereof.

According to another embodiment of the invention, an RFSJ as defined above is disclosed, wherein the jacket comprises at least one opening to permit access to the MRD.

According to another embodiment of the invention, an RFSJ as defined above is disclosed, wherein the opening comprises a reversibly connectable door to permit or restrict access to the MRD though the opening.

According to another embodiment of the invention, an RFSJ as defined above is disclosed, wherein at least a portion of RFSJ comprising a material selected from a group consisting of: thermo insulating material, sealing material, foam material, fire retardant materials, at least partially transparent material and any combination thereof.

According to another embodiment of the invention, an RFSJ as defined above is disclosed, wherein the RFSJ further comprises at least a portion of transparent material. Further the transparent material enables view of at least a portion of the patient/sample accommodated in the MRD. In other embodiments the transparent portion allows light to enter the MRD bore covered by the RFSJ.

According to another embodiment of the invention, an RFSJ as defined above is disclosed, wherein at least a portion of the RFSJ is made of high endurance to impact materials. Such materials are composed from materials such as metal, metal alloys, composite materials and combination thereof. These composites are such as GFRP (glass-fiber reinforced plastic) and CFRP (carbon-fiber reinforced plastic).

According to another embodiment of the invention, an RFSJ as defined above is disclosed, wherein the RFSJ is connected to the MRD operating system.

According to another embodiment of the invention, an RFSJ as defined above is disclosed, wherein the RFSJ comprising modular pieces reversibly connectable to form the RFSJ.

According to another embodiment of the invention, an RFSJ as defined above is disclosed, wherein the RFSJ comprises at least one fastener selected from a group consisting of: a connection between the MRI and the RFSJ, structural integrity of the RFSJ, and any combination thereof.

According to another embodiment of the invention, an RFSJ as defined above is disclosed, wherein at least a portion of the RFSJ comprising channels for passage of a substance selected from a group consisting of: gas, liquid, gel, solid particles, and any combination thereof.

According to another embodiment of the invention, an RFSJ as defined above is disclosed, wherein at least a portion comprises an active thermo regulating system.

According to another embodiment of the invention, an RFSJ as defined above is disclosed, wherein the system is configured to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

According to another embodiment of the invention, an RFSJ as defined above is disclosed, wherein at least a portion of the RFSJ comprising a passive thermo-regulating envelope surrounding an active thermo-regulating system.

According to another embodiment of the invention, an RFSJ as defined above is disclosed, wherein the RFSJ comprises at least one sensor selected from a group consisting of: temperature sensors, EMI sensors, magnetic sensors, vibration sensors, connection sensors, and any combination thereof.

According to another embodiment of the invention, an RFSJ as defined above is disclosed, comprising temperature sensors, wherein the sensors are configured to sense the inner volume temperature, the external environment temperature or both.

According to another embodiment of the invention, an RFSJ as defined above is disclosed, wherein the RFSJ is connected to a component selected from a group consisting of: a CPU, an alarm system, at least one indicator, at least one sensor, and any combination thereof.

According to another embodiment of the invention, an RFSJ as defined above is disclosed, wherein at least a portion comprising a user interface.

According to another embodiment of the invention, an RFSJ as defined above is disclosed, wherein at least a portion comprising an RF detecting system; further wherein the system is connected to at least one selected from a group consisting of: an indicator, an alarm system, a user interface and any combination thereof.

According to another embodiment of the invention, an RFSJ as defined above is disclosed, wherein the RF detection system comprises indicators selected from a group consisting of: audible, sensible, visual and any combination thereof.

According to another embodiment of the invention, an RFSJ as defined above is disclosed, in an atmospheric pressure, temperature changing environment, having at least one first temperature $T_1$ [° C.] and at least one second temperature $T_2$ [° C.], the RFSJ is characterized by: (a) an inner portion fitted by means of size and shape to the external dimensions of the MRD; (b) thermal conductivity, $k$ [W/m ° C.]; (c) thickness, $s$ [m]; and (d) conductive heat transfer, $q$ [W], wherein the following formula is being held true: $q = k\, A\, dT/s$ where $dT$ equals $T_2 - T_1$ and $q \ll 0.01$ W.

According to another embodiment of the invention, an RFSJ as defined above is disclosed, comprising at least n layers, wherein at least 2 of the n layers comprising a substantially different conductive heat transfer value $q$ for each layer; where each of the layers has at least one first temperature $H_1$ [° C.] measured on the outer side of the layer, and at least one first temperature $H_2$ [° C.], measured on its inner side towards the MRD, having a $dH_1 - \ldots dH_n$, where $dT$ of the RFSJ equals $H_1 - H_n$.

According to another embodiment of the invention, an RFSJ as defined above is disclosed, in an MRD being positioned in an atmospheric pressure and a temperature changing environment having at least one first temperature $T_1$ [° C.] and at least one second temperature $T_2$ [° C.], a RFSJ for the MRD, wherein the RFSJ is characterized by a thermal expansion coefficient substantially different than 0.

According to another embodiment of the invention, an RFSJ as defined above is disclosed, comprising at least n layers, wherein at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1 - \ldots dH_n$, where $dT$ of the RFSJ equals $H_1 - H_n$.

According to another embodiment of the invention, an RFSJ as defined above is disclosed, the RFSJ is further characterized by: (a) length $L_{0,\,Jacket}$ [m] fitted by means of size and shape to the $L_{0,MRD}$; and (b) linear thermal expansion coefficient $\alpha_L$ [° C.$^{-1}$] substantially different than 0;

wherein if dT substantially different than 0; the length $L_{0, Jacket}$ will be varied to $L_{1, Jacket}$, such that the formula is being held true for any change in temperature, dT:

$$\alpha_L = \frac{1}{L}\frac{dL}{dT}$$

where dL equals $L_{1, Jacket} - L_{0, Jacket}$ and dT equals $T_2 - T_1$.

According to another embodiment of the invention, an RFSJ as defined above is disclosed, the RFSJ is further characterized by: (a) volume $V_{0\ Jacket}$ [m]; and (b) volumetric thermal expansion coefficient $\alpha_V$ [° C.$^{-1}$] substantially different than 0; wherein if dT substantially different than 0; the volume $V_{0, Jacket}$ will be varied to $V_{1, Jacket}$, such that the formula is being held true for any change in temperature, dT:

$$\alpha_V = \frac{1}{V}\left(\frac{\partial V}{\partial T}\right)$$

where dV equals $V_{1, Jacket} - V_{0, Jacket}$ and dT equals $T_2 - T_1$.

According to another embodiment of the invention, an RFSJ as defined above is disclosed, the jacket is further characterized by: (a) area $A_{0, Jacket}$ [m$^2$]; and (b) area thermal expansion coefficient $\alpha_A$ [° C.$^{-1}$] substantially different than 0; wherein if dT substantially different than 0; the length $A_{0, Jacket}$ will be varied to $A_{1, Jacket}$, such that the formula is being held true for any change in temperature, dT:

$$\alpha_A = \frac{1}{A}\frac{dA}{dT}$$

where dA equals $A_{1, Jacket} - A_{0, Jacket}$ and dT equals $T_2 - T_1$.

According to one embodiment of the invention, a method for RF shielding a magnetic resonance device (MRD), having external dimensions A [m$^2$], and length $L_0$ [m], from electro magnetic interference (EMI), comprising steps of: (a) obtaining an RFSJ sized and shaped to accommodate the MRD; and (b) operating the same; wherein at least a portion of the RFSJ comprises an EMI shield.

According to another embodiment of the invention, a method as defined above is disclosed, additionally comprising a step of shielding at least a portion of the MRD from a selected from a group consisting of: magnetism, electromagnetic interference, physical damage and any combination thereof.

According to another embodiment of the invention, a method as defined above is disclosed, additionally comprising a step of selecting the RFSJ comprising a conduit having at least one first aperture to the MRD bore and at least one aperture to the external environment, fitted for the passage of tubing within; further configuring the conduit to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring the conduit to attenuate electromagnetic interference by means selected from a group consisting of: waveguide, RF filter, waveguide filter, attenuating material, and any combination thereof.

According to another embodiment of the invention, a method as defined above is disclosed, additionally comprising a step of passing tubing though the conduit.

According to another embodiment of the invention, a method as defined above is disclosed, additionally comprising a step of the RFSJ comprises an EMI shield configured to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring the RFSJ for an MRD to be positioned in an atmospheric pressure system and temperature changing environment, having at least one first temperature $T_1$ [° C.] and a Q [kj] amount of heat applied to the same, in which the RFSJ: (a) at least one second temperature $T_2$ [° C.] in the inner portion; (b) a specific mass, m [kg]; and, (c) specific heat capacity, $C_p$ [kj/kg]; wherein the following formula is being held true: $Q = C_p\ m\ dT$; where $dT = T_1 - T_2$, wherein for each applied Q, dT2 is in the range of 0° C.-0.2° C.; where $dT_2 = T_2 + dT$, thereby thermo isolating the MRD.

According to another embodiment of the invention, a method as defined above is disclosed, additionally comprising a step of selecting the RFSJ in which at least a portion of the RFSJ comprises n layers.

According to another embodiment of the invention, a method as defined above is disclosed, additionally comprising a step of selecting the RFSJ in which at least 2 of the n layers comprising a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1 - \ldots\ dHn$, where dT of RFSJ equals $H_1 - Hn$.

According to another embodiment of the invention, a method as defined above is disclosed, additionally comprising a step of shielding at least one layer with shielding means selected from a group consisting of: magnetic shielding, RF shielding, physical shielding and any combination thereof.

According to another embodiment of the invention, a method as defined above is disclosed, additionally comprising a step of electrically isolating the RFSJ within at least one layer.

According to another embodiment of the invention, a method as defined above is disclosed, additionally comprising a step of closing a conductive circle around the MRD with at least one layer.

According to another embodiment of the invention, a method as defined above is disclosed, additionally comprising a step of selecting at the RFSJ with at least a portion of conductive coating, or conductive plating.

According to another embodiment of the invention, a method as defined above is disclosed, additionally comprising a step of selecting the RFSJ in which at least a portion of having a material selected from a group consisting of: metal, metal containing composite, metal containing foam, metallic plastic composite and any combination thereof.

According to another embodiment of the invention, a method as defined above is disclosed, additionally comprising a step of selecting the RFSJ having at least a portion of selected from a group consisting of: a metallic plate, a metallic mesh, a metallic web, a perforated metallic plate, a metallic wire interlace and any combination thereof.

According to another embodiment of the invention, a method as defined above is disclosed, additionally comprising a step of selecting the RFSJ having at least one opening to permit access to the MRD.

According to another embodiment of the invention, a method as defined above is disclosed, additionally comprising a step of opening or closing the opening with a door.

According to another embodiment of the invention, a method as defined above is disclosed, additionally comprising a step of selecting the RFSJ having at least a portion of a material selected from a group consisting of: thermo insulating material, sealing material, foam material, fire retardant materials, at least partially transparent material and any combination thereof.

According to another embodiment of the invention, a method as defined above is disclosed, additionally comprising a step of connecting the RFSJ to the MRD operating system.

According to another embodiment of the invention, a method as defined above is disclosed, additionally comprising a step of reversibly connecting modular pieces to form the RFSJ.

According to another embodiment of the invention, a method as defined above is disclosed, additionally comprising a step of securing the RFSJ with at least one fastener, selected from a group consisting of: a connection between the MRI and the RFSJ, structural integrity of the RFSJ, and any combination thereof.

According to another embodiment of the invention, a method as defined above is disclosed, additionally comprising a step of selecting the RFSJ having at least a portion of with channels for passage of a substance selected from a group consisting of: gas, liquid, gel, solid particles or any combination thereof.

According to another embodiment of the invention, a method as defined above is disclosed, additionally comprising a step of passing a substance selected from a group consisting of: gas, liquid, gel, solid particles or any combination thereof, in the channels.

According to another embodiment of the invention, a method as defined above is disclosed, additionally comprising a step of operating an active thermo regulating system.

According to another embodiment of the invention, a method as defined above is disclosed, additionally comprising a step of configuring the system to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

According to another embodiment of the invention, a method as defined above is disclosed, additionally comprising a step of selecting the RFSJ having at least a portion of comprising a passive thermo-regulating envelope surrounding an active thermo-regulating system.

According to another embodiment of the invention, a method as defined above is disclosed, additionally comprising a step of selecting the RFSJ having at least one sensor selected from a group consisting of: temperature sensors, EMI sensors, magnetic sensors, vibration sensors, connection sensors, and any combination thereof.

According to another embodiment of the invention, a method as defined above is disclosed, additionally comprising a step of configuring the sensors to sense the inner volume temperature, the external environment temperature or both.

According to another embodiment of the invention, a method as defined above is disclosed, additionally comprising a step of selecting the RFSJ comprising a component selected from a group consisting of: user interface, an RF detection system, A CPU, an alarm system, at least one indicator, and any combination thereof.

According to another embodiment of the invention, a method as defined above is disclosed, additionally comprising a step of connecting and operating the RF detection system to a component selected from a group consisting of: at least one indicator, at least one sensor, user interface, display, an alarm system, and any combination thereof.

According to another embodiment of the invention, a method as defined above is disclosed, additionally comprising a step of connecting the RFSJ to a component selected from a group consisting of: a CPU, an alarm system, at least one indicator, at least one sensor, and any combination thereof.

According to another embodiment of the invention, a method as defined above is disclosed, additionally comprising a step of configuring the RFSJ for an MRD to be positioned in an atmospheric pressure, temperature changing environment, having at least one first temperature $T_1$ [° C.] and at least one second temperature $T_2$ [° C.], in which the RFSJ: (a) thermal conductivity, k [W/m ° C.]; (b) thickness, s [m]; and, (c) conductive heat transfer, q [W]; wherein the following formula is being held true: q=k A dT/s, where dT equals $T_2-T_1$ and q<<0.01 W, thereby thermo isolating the MRD.

According to another embodiment of the invention, a method as defined above is disclosed, additionally comprising a step of selecting the RFSJ having at least n layers, in which at least 2 of the n layers comprising a substantially different conductive heat transfer value q for each layer; in which each of the layers has at least one first temperature $H_1$ [° C.] measured on the outer side of the layer, and at least one first temperature $H_2$ [° C.], measured on its inner side towards the MRD, having a $dH_1- \ldots dHn$, where dT of the RFSJ equals $H_1-Hn$.

According to another embodiment of the invention, a method as defined above is disclosed, additionally comprising a step of, configuring the RFSJ for an MRD being positioned in an atmospheric pressure and a temperature changing environment having at least one first temperature $T_1$ [° C.] and at least one second temperature $T_2$ [° C.], a RFSJ for the MRD, in which the RFSJ is characterized by a thermal expansion coefficient substantially different than 0.

According to another embodiment of the invention, a method as defined above is disclosed, additionally comprising a step of selecting the RFSJ having at least n layers, in which at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1- \ldots dHn$, where dT of the RFSJ equals $H_1-Hn$.

According to another embodiment of the invention, a method as defined above is disclosed, additionally comprising a step of selecting the RFSJ in which: (a) length $L_{0,\,Jacket}$ [m] fitted by means of size and shape to the $L_{0,MRD}$; and (b) linear thermal expansion coefficient $\alpha_L$ [° C.$^{-1}$] substantially different than 0; wherein if dT substantially different than 0; the length $L_{0,\,Jacket}$ will be varied to $L_{1,\,Jacket}$, such that the formula is being held true for any change in temperature, dT:

$$\alpha_L = \frac{1}{L}\frac{dL}{dT}$$

where dL equals $L_{1,\ Jacket} - L_{0,\ Jacket}$ and dT equals $T_2-T_1$, thereby thermo isolating the MRD.

According to another embodiment of the invention, a method as defined above is disclosed, additionally comprising a step of selecting the RFSJ in which: (a) volume $V_{0\ Jacket}$ [m]; and (b) volumetric thermal expansion coefficient $\alpha_V$ [° C.$^{-1}$] substantially different than 0; wherein if dT substantially different than 0; the volume $V_{0,\ Jacket}$ will be varied to $V_{1,\ Jacket}$, such that the formula is being held true for any change in temperature, dT:

$$\alpha_V = \frac{1}{V}\left(\frac{\partial V}{\partial T}\right)$$

where dV equals $V_{1,\ Jacket} - V_{0,Jacket}$ and dT equals $T_2-T_1$, thereby thermo isolating the MRD.

According to another embodiment of the invention, a method as defined above is disclosed, additionally comprising a step of selecting the RFSJ in which: (a) area $A_{0,\ Jacket}$ [m$^2$]; and, (b) area thermal expansion coefficient $\alpha_A$ [° C.$^{-1}$] substantially different than 0; wherein if dT substantially different than 0; the length $A_{0,\ Jacket}$ will be varied to $A_{1,\ Jacket}$, such that the formula is being held true for any change in temperature, dT:

$$\alpha_A = \frac{1}{A}\frac{dA}{dT}$$

where dA equals $A_{1,\ Jacket} - A_{0,\ Jacket}$ and dT equals $T_2-T_1$, thereby thermo isolating the MRD.

According to one embodiment of the invention, a method for manufacturing an RFSJ for a magnetic resonance device (MRD), having external dimensions A [m$^2$], and length $L_0$ [m], from electro magnetic interference (EMI), comprising steps of: (a) sizing and shaping the RFSJ fitting to accommodate the MRD; and (b) forming the RFSJ; wherein the step of forming the RFSJ in which at least a portion of comprises an EMI shield.

According to another embodiment of the invention, a method as defined above is disclosed, additionally comprising a step of shielding at least a portion of the MRD from a force selected from a group consisting of: magnetism, electromagnetic interference, physical damage and any combination thereof.

According to another embodiment of the invention, a method as defined above is disclosed, additionally comprising a step of constructing the RFSJ comprising a conduit having at least one first aperture to the MRD bore and at least one aperture to the external environment, fitted for the passage of tubing within; further configuring the conduit to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring the conduit to attenuate electromagnetic interference by means selected from a group consisting of: waveguide, RF filter, waveguide filter, attenuating material, and any combination thereof.

According to another embodiment of the invention, a method as defined above is disclosed, additionally comprising a step of passing tubing though the conduit.

According to another embodiment of the invention, a method as defined above is disclosed, additionally comprising a step of the RFSJ comprises an EMI shield configured to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring the MRD to be positioned in an atmospheric pressure system and temperature changing environment, having at least one first temperature $T_1$ [° C.] and a Q [kj] amount of heat applied to the same, in which the RFSJ: (a) at least one second temperature $T_2$ [° C.] in the inner portion; (b) a specific mass, m [kg]; and, specific heat capacity, $C_p$ [kj/kg]; wherein the following formula is being held true: $Q=C_p$ m dT; where $dT=T_1-T_2$, wherein for each applied Q, dT2 is in the range of 0° C.-0.2° C.; where $dT_2=T_2+dT$, thereby thermo isolating the MRD.

According to another embodiment of the invention, a method as defined above is disclosed, additionally comprising a step of constructing the RFSJ in which at least a portion of the RFSJ comprises n layers.

According to another embodiment of the invention, a method as defined above is disclosed, additionally comprising a step of constructing the RFSJ having at least 2 of the n layers in which a substantially different specific heat capacity $C_p$ for each layer; where each of the layers has at least one first temperature $H_1$ [° C.] measured on the outer side of the layer, and at least one first temperature $H_2$ [° C.], measured on its inner side towards the MRD, having a $dH_1$- ... dHn, where dT of RFSJ equals $H_1$–Hn.

According to another embodiment of the invention, a method as defined above is disclosed, additionally comprising a step of shielding at least one layer with shielding means selected from a group consisting of: magnetic shielding, RF shielding, physical shielding and any combination thereof.

According to another embodiment of the invention, a method as defined above is disclosed, additionally comprising a step of electrically isolating the RFSJ with at least one layer.

According to another embodiment of the invention, a method as defined above is disclosed, additionally comprising a step of closing a conductive circle around the MRD with at least one layer.

According to another embodiment of the invention, a method as defined above is disclosed, additionally comprising a step of coating or plating at least a portion of the RFSJ with a conductive material.

According to another embodiment of the invention, a method as defined above is disclosed, additionally comprising a step of forming the RFSJ in which at least a portion of having a material selected from a group consisting of: metal, metal containing composite, metal containing foam, metallic plastic composite and any combination thereof.

According to another embodiment of the invention, a method as defined above is disclosed, additionally comprising a step of forming at least a portion of the RFSJ with a material selected from a group consisting of: a metallic plate, a metallic mesh, a metallic web, a perforated metallic plate, a metallic wire interlace and any combination thereof.

According to another embodiment of the invention, a method as defined above is disclosed, additionally comprising a step of forming at least one opening in RFSJ permitting access to the MRD.

According to another embodiment of the invention, a method as defined above is disclosed, additionally comprising a step of connecting a maneuverable door to the opening permitting or restricting access to the opening.

According to another embodiment of the invention, a method as defined above is disclosed, additionally comprising a step of forming the RFSJ having at least a portion of a material selected from a group consisting of: thermo insulating material, sealing material, foam material, fire retardant materials, at least partially transparent material and any combination thereof.

According to another embodiment of the invention, a method as defined above is disclosed, additionally comprising a step of connecting the RFSJ to the MRD operating system.

According to another embodiment of the invention, a method as defined above is disclosed, additionally comprising a step of forming modular pieces reversibly connecting to construct the RFSJ.

According to another embodiment of the invention, a method as defined above is disclosed, additionally comprising a step of connecting at least one fastener to secure a selected from a group consisting of: a connection between the MRI and the RFSJ, structural integrity of the RFSJ, and any combination thereof.

According to another embodiment of the invention, a method as defined above is disclosed, additionally comprising a step of forming at least a portion of the RFSJ with channels for passage of a substance selected from a group consisting of: gas, liquid, gel, solid particles or any combination thereof.

According to another embodiment of the invention, a method as defined above is disclosed, additionally comprising a step of passing a substance selected from a group consisting of: gas, liquid, gel, solid particles or any combination thereof, in the channels.

According to another embodiment of the invention, a method as defined above is disclosed, additionally comprising a step of connecting an active thermo regulating system to the RFSJ.

According to another embodiment of the invention, a method as defined above is disclosed, additionally comprising a step of configuring the system to a setting selected from a group consisting of: maintain a predetermined temperature, operate only when a predetermined temperature has been measured within the inner volume, respond to temperature changes in the external environment, operate only within a predetermined temperature range, shut down at a predetermined temperature and any combination thereof.

According to another embodiment of the invention, a method as defined above is disclosed, additionally comprising a step of constructing the RFSJ having at least a portion of comprising a passive thermo-regulating envelope surrounding an active thermo-regulating system.

According to another embodiment of the invention, a method as defined above is disclosed, additionally comprising a step of connecting at least one sensor to the RSFJ selected from a group consisting of: temperature sensors, EMI sensors, magnetic sensors, vibration sensors, connection sensors, and any combination thereof.

According to another embodiment of the invention, a method as defined above is disclosed, additionally comprising a step of configuring the sensors to sense the inner volume temperature, the external environment temperature or both.

According to another embodiment of the invention, a method as defined above is disclosed, additionally comprising a step of connecting a component selected from a group consisting of: user interface, an RF detection system, A CPU, an alarm system, at least one indicator, and any combination thereof, to the RFSJ.

According to another embodiment of the invention, a method as defined above is disclosed, additionally comprising a step of connecting the RF detection system to a component selected from a group consisting of: at least one indicator, at least one sensor, user interface, display, an alarm system, and any combination thereof.

According to another embodiment of the invention, a method as defined above is disclosed, additionally comprising a step of connecting the RFSJ to a component selected from a group consisting of: a CPU, an alarm system, at least one indicator, at least one sensor, and any combination thereof.

According to another embodiment of the invention, a method as defined above is disclosed, additionally comprising a step of configuring the RFSJ for an MRD to be positioned in an atmospheric pressure, temperature changing environment, having at least one first temperature $T_1$ [° C.] and at least one second temperature $T_2$ [° C.], in which the RFSJ: (a) thermal conductivity, k [W/m ° C.]; (b) thickness, s [m]; and, (c) conductive heat transfer, q [W]; wherein the following formula is being held true: q=k A dT/s, where dT equals $T_2-T_1$ and q<<0.01 W, thereby thermo isolating the RFSJ.

According to another embodiment of the invention, a method as defined above is disclosed, additionally comprising a step of constructing the RFSJ having at least n layers, in which at least 2 of the n layers comprising a substantially different conductive heat transfer value q for each layer; in which each of the layers has at least one first temperature $H_1$ [° C.] measured on the outer side of the layer, and at least one first temperature $H_2$ [° C.], measured on its inner side towards the MRD, having a $dH_1- \ldots dHn$, where dT of the RFSJ equals $H_1-Hn$.

According to another embodiment of the invention, a method as defined above is disclosed, additionally comprising a step of, configuring the RFSJ for an MRD being positioned in an atmospheric pressure and a temperature changing environment having at least one first temperature $T_1$ [° C.] and at least one second temperature $T_2$ [° C.], a RFSJ for the MRD, in which the RFSJ is characterized by a thermal expansion coefficient substantially different than 0.

According to another embodiment of the invention, a method as defined above is disclosed, additionally comprising a step of selecting the RFSJ having at least n layers, in which at least 2 of the n layers comprising a substantially different thermal expansion coefficient for each layer; where each of the layers has at least one first temperature $H_1$ [° C.] measured on the outer side of the layer, and at least one first temperature $H_2$ [° C.], measured on its inner side towards the MRD, having a $dH_1- \ldots dHn$, where dT of the RFSJ equals $H_1-Hn$.

According to another embodiment of the invention, a method as defined above is disclosed, additionally comprising a step of forming the RFSJ in which: (a) length $L_{0, Jacket}$ [m] fitted by means of size and shape to the $L_{0, MRD}$; and, (b) linear thermal expansion coefficient $\alpha_L$ [° C.$^{-1}$] substantially different than 0; wherein if dT substantially different than 0; the length $L_{0, Jacket}$ will be varied to $L_{1, Jacket}$, such that the formula is being held true for any change in temperature, dT:

$$\alpha_L = \frac{1}{L}\frac{dL}{dT}$$

where dL equals $L_{1, Jacket}-L_{0, Jacket}$ and dT equals $T_2-T_1$, thereby thermo isolating the MRD.

According to another embodiment of the invention, a method as defined above is disclosed, additionally comprising a step of forming the RFSJ in which: (a) volume $V_{0\ Jacket}$ [m]; and (b) volumetric thermal expansion coefficient $\alpha_V$ [° $C.^{-1}$] substantially different than 0; wherein if dT substantially different than 0; the volume $V_{0,\ Jacket}$ will be varied to $V_{1,\ Jacket}$, such that the formula is being held true for any change in temperature, dT:

$$\alpha_V = \frac{1}{V}\left(\frac{\partial V}{\partial T}\right)$$

where dV equals $V_{1,\ Jacket}-V_{0,Jacket}$ and dT equals $T_2-T_1$, thereby thermo isolating the MRD.

According to another embodiment of the invention, a method as defined above is disclosed, additionally comprising a step of forming the RFSJ in which: (a) area $A_{0,\ Jacket}$ [m²]; and, (b) area thermal expansion coefficient $\alpha_A$ [° $C.^{-1}$] substantially different than 0; wherein if dT substantially different than 0; the length $A_{0,\ Jacket}$ will be varied to $A_{1,\ Jacket}$, such that the formula is being held true for any change in temperature, dT:

$$\alpha_A = \frac{1}{A}\frac{dA}{dT}$$

where dA equals $A_{1,\ Jacket}-A_{0,\ Jacket}$ and dT equals $T_2-T_1$, thereby thermo isolating the MRD.

Reference is now made to FIG. 1A schematically illustrating, in an out of scale manner, an embodiment of the invention. The rectangular embodiment of a RFSJ (100) completely encasing an MRD (800). In this embodiment the jacket is constructed from two pieces presented by the dividing horizontal line (80), thereby enabling insertion of the MRD into the jacket. In this embodiment the RFSJ encloses an electric circuit around the MRD. Additionally or alternatively, at least a portion of the RFSJ is made with electrical conductive materials, forming a faraday cage. Additionally or alternatively, the RFSJ is constructed in layers, such that at least one of the layers is electrically conductive. Additionally or alternatively, the RFSJ comprises sensors such as temperature sensors, RF sensors, electrical sensors, etc., connected to a CPU, or an alarm system. Additionally or alternatively, the thermo isolating jacket acts as a passive electromagnetic shield. This can be achieved by means of forming the jacket as a casing (100) of conductive material or mesh thereby creating a faraday cage. Another option is that the jacket (100) is coated with metal containing spray, metal plated, or constructed with conductive compound materials. In order to create an effective non-active magnetic shielding at least a portion of the jacket is constructed from magnetic alloys with high permeability and low coercivity such as Permalloy, and different types of Mu-metal. These are constructed from elements such as metal sheet, metal casting, metal screen, metal containing foam, metallic ink and any combination thereof. Further taking into consideration the possibility of creating Eddy currents, the jacket can be constructed with thin plates of conductive material, with metal coating or combined with capacitors to help dissipate these currents. Additionally or alternatively, the jacket comprises an EMI shield configured to attenuate the passage of frequencies selected from a group consisting of: 0 to about 1000 MHz, 0 to about 500 MHz, 0 to about 200 MHz and any combination thereof. Additionally or alternatively the jacket comprises means for shielding from physical damage such as including strong shock absorptive materials, fluid isolating materials, non-abrasive coating, etc. Additionally or alternatively, the RFSJ is thermo isolating the MRD from the external environment temperature. This is achieved by constructing the RFSJ with materials such as sealing materials, thermo-isolating materials, and materials with thermal mass properties facilitating in absorbing the temperature changes. Additionally or alternatively, the RFSJ is combined with fire resistant materials. Additionally or alternatively, the RFSJ comprises embedded or connected sensors such as temperature, RF, magnetic, vibration, etc., sensing a quality in the MRD, the RFSJ, the external environment or any combination thereof. These sensors can further be connected to indicators (auditable, sensible, or visual) and to a CPU, an alarm system, a user interface or any combination thereof.

Figure 1B:
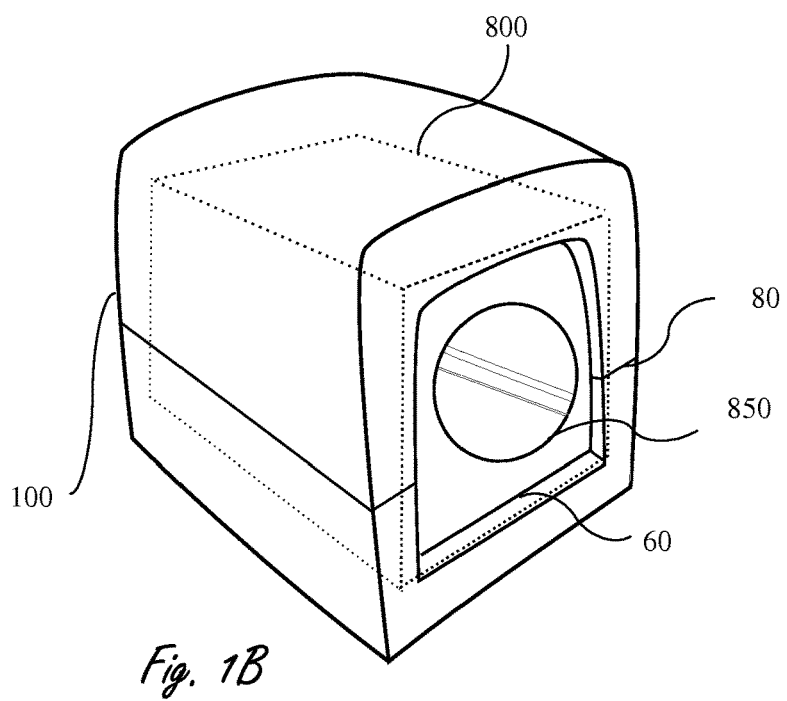
FIG. 1B is a schematic illustration of an MRD RFSJ comprising an opening.

Reference is now made to FIG. 1B schematically illustrating, in an out of scale manner, an embodiment of the invention. An embodiment of a RF shielding jacket (100), encasing an MRD (800), having an opening (60) to enable access to the MRD bore (850). In this embodiment the RFSJ is constructed from two pieces presented by the dividing vertical line (80), thereby enabling insertion of the MRD into the RF shielding jacket. Additionally or alternatively, this opening is closeable by a panel maintaining the RF shielding properties.

Figure 2:
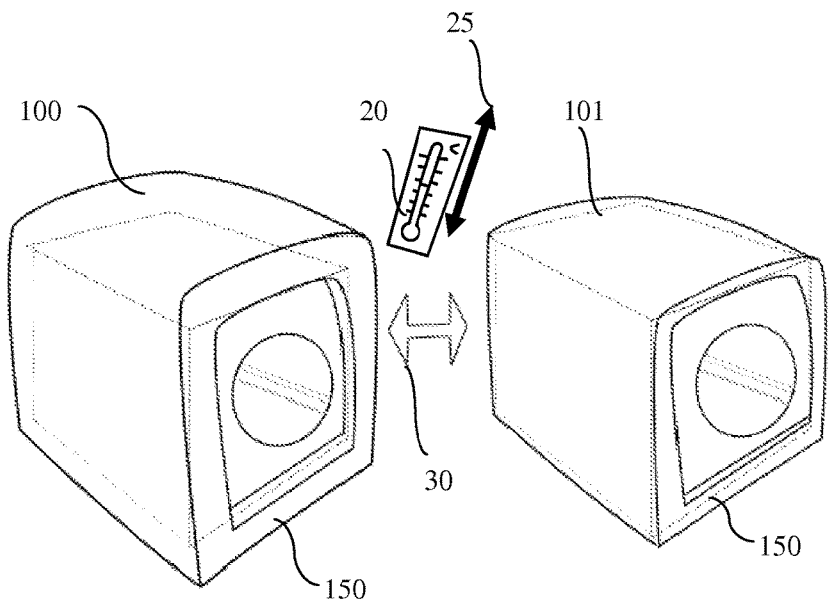
FIG. 2 is a schematic illustration of an MRD RFSJ comprising thermal mass expansion properties.
Figures 3A, 3B:
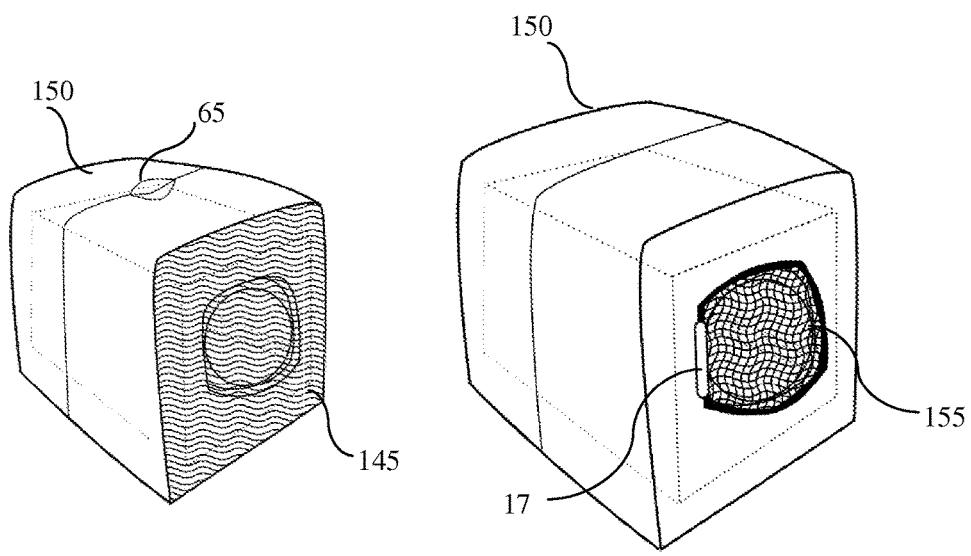
FIG. 3A is a schematic illustration of an MRD RFSJ embodied having a portion of a mesh construction.
FIG. 3B is a schematic illustration of an MRD RFSJ embodied comprising a wire interlace maneuverable door.

Reference is now made to FIG. 2 schematically illustrating, in an out of scale manner, an embodiment of the invention. In this embodiment a RF shielding jacket (101) is encasing an MRD (150). This MRD comprises at least a portion of a material with thermal expansion properties so that the thermal expansion co-efficient in substantially different than 0. As the temperature measured (20) of the environment changes (25), the surface area properties of the RFSJ change (30), for example grow to a different size (100) depending on the temperature change, and so the temperature of the MRD remains relatively stable in reference to the environment temperature. In an embodiment the temperature change could be manifested in the RFSJ in thermal mass expansion or compression that can be measured linearly, volumetrically, or by measuring change in the surface area. Additionally or alternatively, this opening is closeable by a panel maintaining the RF shielding properties Reference is now made to FIG. 3A schematically illustrating, in an out of scale manner, an embodiment of the invention. In this embodiment the RF shielding jacket (100) encasing the MRD (800), has a portion of a mess material (145) functioning as a panel of the RFSJ, maintain the RF shielding properties of the jacket. Additionally or alternatively, this portion is perforated, to allow passage of air or light, but not EMI to and from the MRD.

Reference is now made to FIG. 3B schematically illustrating, in an out of scale manner, an embodiment of the invention. In this embodiment the RF shielding jacket (100) is encasing the MRD (800), having an opening (60) providing access to the MRD bore. The opening is connected to a door made out of a wire interlace (155) by a maneuverable element such as a hinge (17). The RF shielding jacket provides a placement for the MRD that is also thermo isolating.

Figure 4:
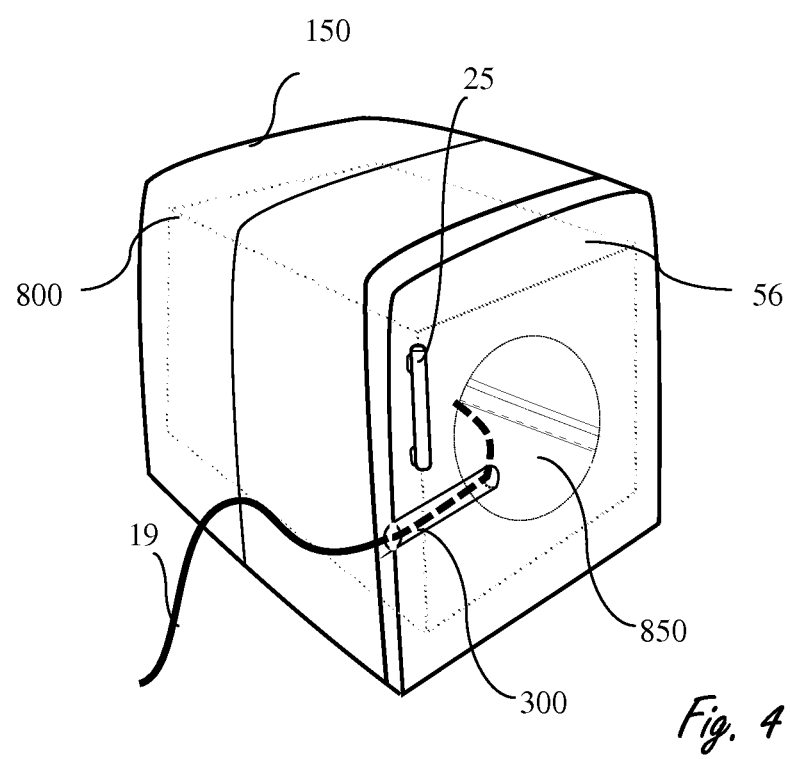
FIG. 4 is a schematic illustration of an MRD RFSJ comprising a RF shielding conduit.

Reference is now made to FIG. 4 schematically illustrating, in an out of scale manner, an embodiment of the invention. The rectangular embodiment of a RF shielding jacket (150) encasing an MRD (800). In this embodiment the RF shielding jacket comprises a sealable door (56) with a handle (25). The door is connected with a maneuverable element such as a hinge, a pivot point, a sliding mechanism, a joint, telescopic arms, and etc., to either permit or restrict access to the opening. Additionally or alternatively, the door (56) harbors an RF shielding conduit (300) sized and shaped for the passage of tubing (19) from the MRD bore (850) to the external environment and contrariwise. The conduit having at least one first aperture to the MRD bore (850) and at least one aperture to the external environment, is configured to attenuate the passage of frequencies selected from a group consisting of: 0 to about 1000 MHz, 0 to about 500 MHz, 0 to about 200 MHz and any combination thereof. Additionally or alternatively, the RFSJ and the connected door (56) comprises at least a portion of thermo isolating material. Further, the door harbors isolating lining such as rubber or foam to further isolate the connecting contour. Additionally or alternatively the jacket comprises a manual or automatic mechanism for opening and closing the door. Additionally or alternatively, the thermo isolating jacket acts as a passive electromagnetic shield. This can be achieved by means of forming the jacket as a casing (100) of conductive material or mesh thereby creating a faraday cage. In this embodiment the door (56) is also made with at least a portion of metallic material or compound. Another option is that the jacket (100) and the door (56) are coated with metal containing spray, metal plated, or constructed with conductive compound materials. In order to create an effective non-active magnetic shielding at least a portion of the jacket is constructed from magnetic alloys with high permeability and low coercivity such as Permalloy, and different types of Mu-metal. These are constructed from elements such as metal sheet, metal casting, metal screen, metal containing foam, metallic ink and any combination thereof. Further taking into consideration the possibility of creating Eddy currents, the jacket can be constructed with thin plates of conductive material, with metal coating or combined with capacitators to help dissipate these currents. Additionally or alternatively, the jacket comprises an EMI shield configured to attenuate the passage of frequencies selected from a group consisting of: 0 to about 1000 MHz, 0 to about 500 MHz, 0 to about 200 MHz and any combination thereof. Additionally or alternatively the jacket comprises means for shielding from physical damage such as including strong shock absorptive materials, fluid isolating materials, non-abrasive coating, etc.

Figure 5:
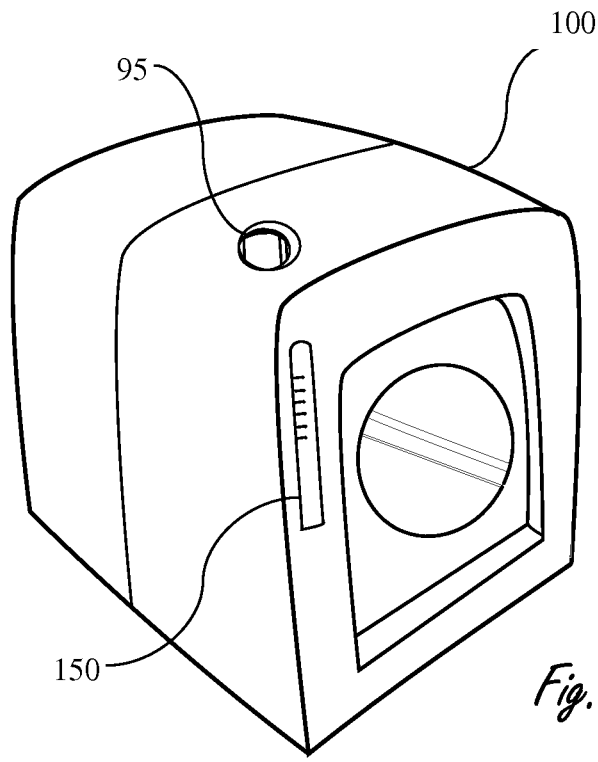
FIG. 5 is a schematic illustration of an MRD RFSJ embodied comprising a container.

Reference is now made to FIG. 5 schematically illustrating, in an out of scale manner, an embodiment of the invention. The rectangular embodiment of a RF shielding jacket (100) encasing an MRD. In this embodiment the RF shielding jacket comprises a container for such as fluid, gel, solid particles, gas, etc., with an opening (95) to fill liquid, gas, gel, small solid particles, etc., and a meter to assess status thereof (temperature, volume, composition etc.). Additionally or alternatively, the RFSJ comprises a display (150) for such as the temperature of the MRD, the amount of material in the container and etc. This embodiment contains a closeable panel to restrict access to the MRD bore and to maintain RF shielding properties.

Figure 6:
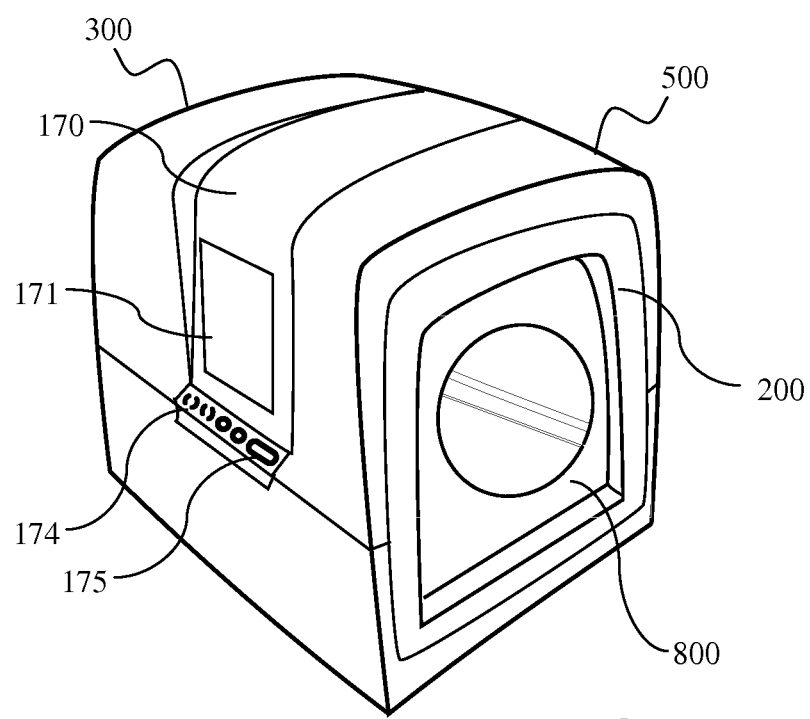
FIG. 6 is a schematic illustration of an MRD RFSJ embodied as nested shells comprising an active thermo-regulating system enclosed by a passive temperature regulation system.

Reference is now made to FIG. 6 schematically illustrating, in an out of scale manner, an embodiment of the invention. In this embodiment the RF shielding jacket (100) is embodied as nested shells comprising an active thermo-regulating system (200) enclosed by a passive thermo-regulating system (500), in addition to it RF shielding properties. In this embodiment, an active thermo-regulating system's engine is placed in the back portion of the RFSJ (300). In other embodiments the engine resides externally to the jacket. This embodiment further harbors a user interface module (170) having a display screen (171), indicators (174) and operating buttons (175); To achieve RF shielding the opening is further covered by a panel or a reversibly connected door, closing a conductive circuit. Additionally or alternatively a CPU connected within the RFSJ controls all output of embedded sensors (temperature, EMI, vibration, etc.) to a display, and allows control of the active thermo regulating system, the MRD operating system or both. At least one layer contains electrically conductive materials and closes a faraday cage when shut by an appropriate panel.

Figure 7A:
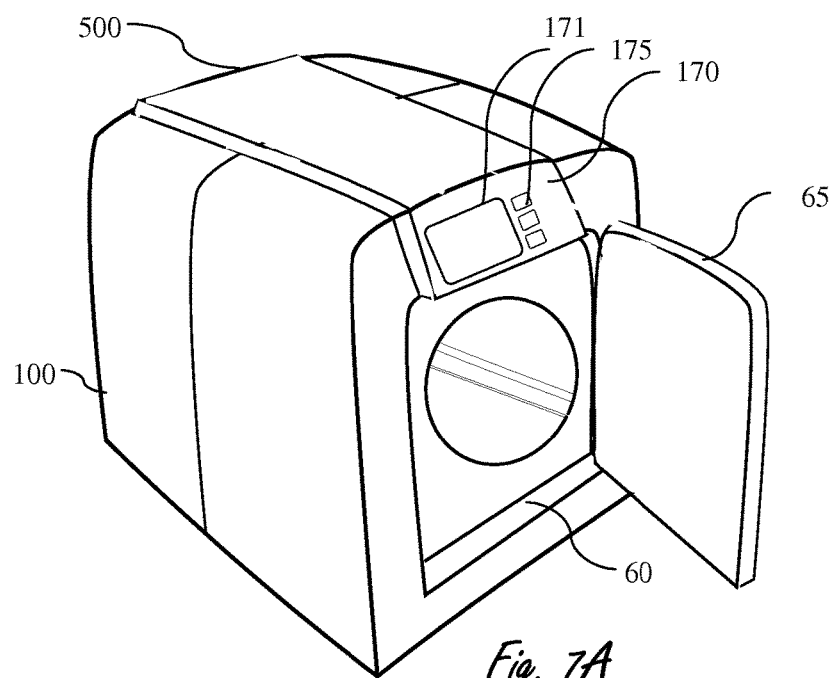
FIG. 7A is a schematic illustration of an MRD RFSJ embodied comprising a fastener and a front facing user interface.

Reference is now made to FIG. 7A schematically illustrating, in an out of scale manner, an embodiment of the invention. In this embodiment the MRD RF shielding jacket (100) comprises a fastener part (500) holding the parts of the RF shielding jacket together with the MRD, and a front facing user interface (170) having a display screen (171) and indicators (172); the indicators can be audible, visual, or sensory. In an embodiment the user interface is configured to control the MRD. In addition, this embodiment comprises a reversibly connected panel or door (65) closing an opening (60) in the jacket providing accesses to the MRD. Additionally or alternatively, there is an additional fastener connecting the assembly of MRD and RFSJ together.

Figure 7B:
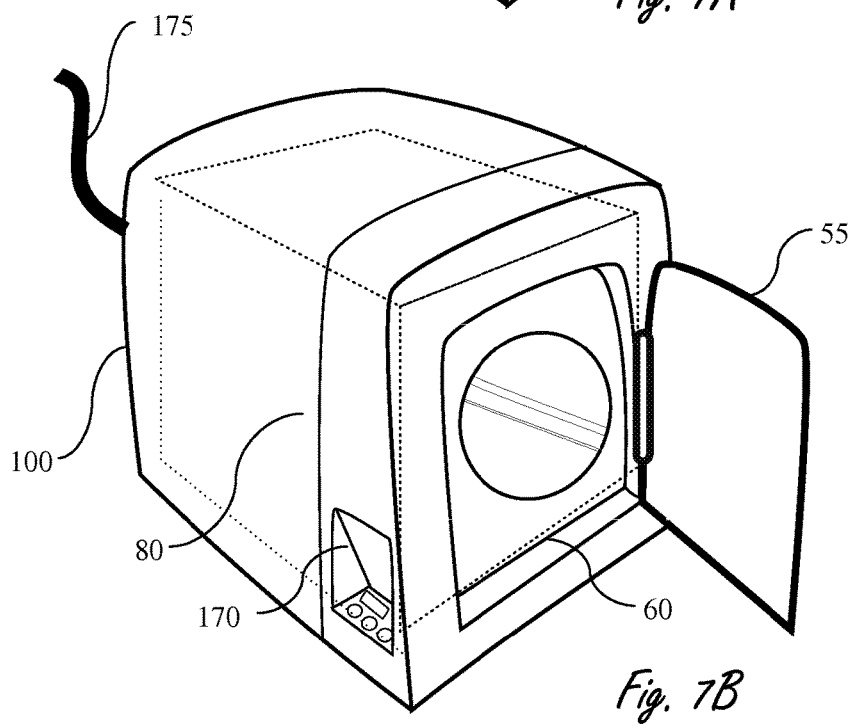
FIG. 7B is a schematic illustration of an MRD RFSJ embodied comprising a side facing user interface.

Reference is now made to FIG. 7B schematically illustrating, in an out of scale manner, an embodiment of the invention. In this embodiment the MRD RF shielding jacket (100) comprises two unequal parts divided by the vertical line (80), and a side facing user interface (170) having a display screen (171), and an alarm system harboring indicators (visual, audible, sensible), and indicators (viewable indicators, auditable indicators, sensible indicators) (172); In an embodiment the alarm system is connected to a component selected from a group consisting of: sensors, visual indicators, audible indicators, sensible indicators, CPU, power supply, user interface, and any combination thereof. In an embodiment, the user interface further harbors an element such as control buttons, handles. In an embodiment the RF shielding jacket is connected to a power supply that is internally supplied DC, externally supplied AC or DC (175) or both. In addition this embodiment harbors a maneuverably connected door (55) to shut an opening (60) in the RF shielding jacket.

Figure 8:
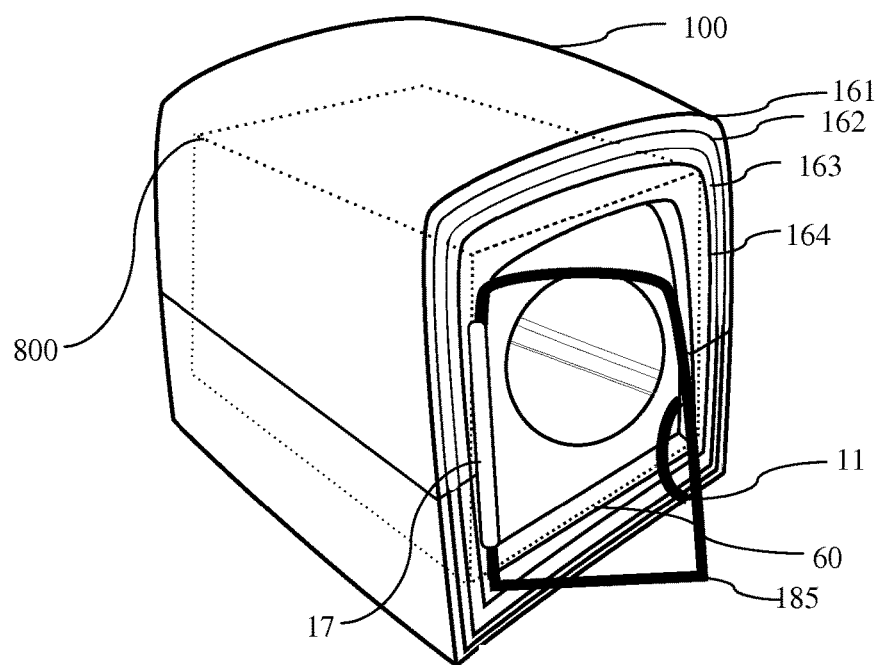
FIG. 8 is a schematic illustration of an MRD RFSJ embodied comprising a hinged door.

Reference is now made to FIG. 8 schematically illustrating, in an out of scale manner, an embodiment of the invention. In this embodiment the RF shielding jacket (100) encasing an MRD (800) has an opening (60) permitting access to the MRD bore. The opening has a maneuverable connection (17) with a component such as a hinge, connecting an at least partly transparent door (185), to either permit or restrict access to the opening, having a handle (11). This access is to such as the bore of the MRD, to the user interface of the MRD, to the connection of the MRD to third party elements, to the connections of the MRD to electricity, etc. In this embodiment the RF shielding jacket comprises a multilayered construction (161, 162, 163, and 164). Additionally or alternatively, at least one layer comprising a conducting portion providing RF shielding (161). Additionally or alternatively, at least one layer comprising passive thermo isolating material (162). Additionally or alternatively, at least one layer comprising a substantially different specific heat capacity Cp (163) than another layer (162). Additionally or alternatively, at least one layer comprising a substantially different conductive heat transfer value q (164) than a previous layer (163).

Figure 9:
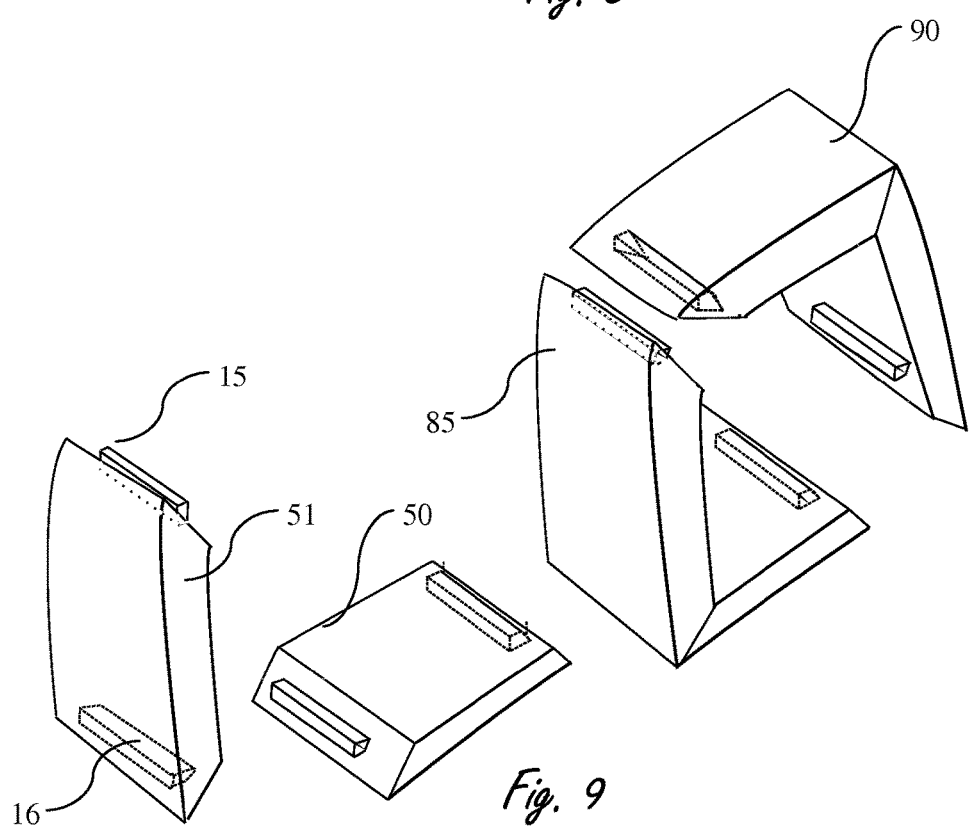
FIG. 9 is a schematic illustration of an embodiment of connectable parts of the MRD RFSJ.

Reference is now made to FIG. 9 schematically illustrating, in an out of scale manner, an embodiment of the invention. In this embodiment the RFSJ is comprised from modular pieces (50, 51), that have a projection (15) that fits in a designated socket (16). This embodiment enables disassembly of the jacket by the user and enables minimizing the storage space of the RFSJ. The figure shoes parts (50) and (51) combining into pieces (85) and (90) as an example of construction. Further the RF shielding jacket can be foldable. Additionally or alternatively, the modular pieces are provided having different properties like for example different thermo isolating properties (heat conduction rate, thermal mass properties, thermal capacity), fluid sealing, wind proofing, magnetic shielding, physical shielding, EMI shielding, and etc. Additionally or alternatively, different size modular pieces are provided. Additionally or alternatively other means of connecting the modular pieces are available such as connection with a maneuverable connection such as a hinge, joint, sliding rails, hook, ball and socket, snip, pin, zipper, or any connecting as disclosed above. Additionally or alternatively, the modular pieces comprise openings.

Figure 10A:
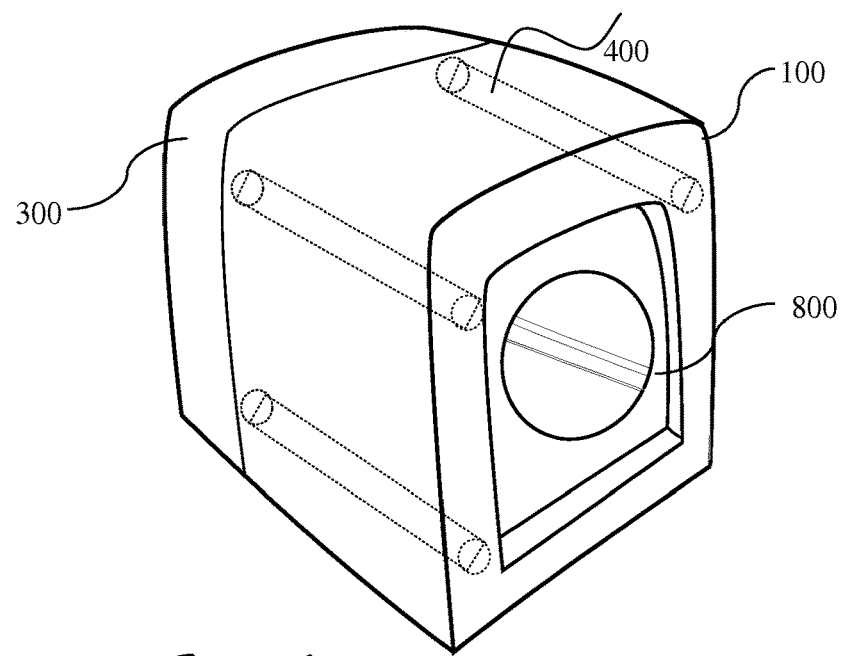
FIG. 10A is a schematic illustration of an MRD RFSJ embodied as comprising channels for thermo-regulating.

Reference is now made to FIG. 10A schematically illustrating, in an out of scale manner, an embodiment of the invention. In this invention the RF shielding jacket (100) comprises horizontal channels (400) for thermo-regulating the MRD. These channels are further connected to an active thermo-regulating system located within (300). The active system is connected to a power supply that is internally supplied DC, externally supplied AC or DC or both.

Figure 10B:
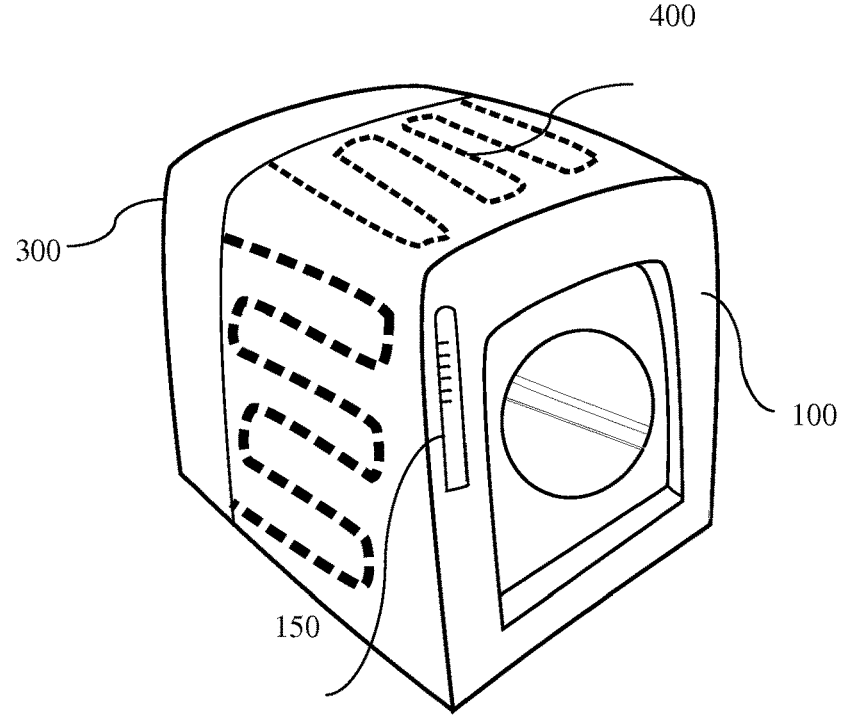
FIG. 10B is a schematic illustration of an MRD RFSJ embodied comprising channels for thermo-regulating.

Reference is now made to FIG. 10B schematically illustrating, in an out of scale manner, an embodiment of the invention. The rectangular embodiment of a RF shielding jacket (100) comprising an active thermo-regulating system, harboring a thermo-regulating mechanism in the back portion (300) and comprising channels (400) for the passage of liquid and/or gas thermo-regulating, connected to this mechanism and passing along the MRD within the RF shielding jacket. This embodiment further comprises an indicator (150) for temperature of the RF shielding jacket inner volume.

Reference is now made to FIG. 11A schematically illustrating, in an out of scale manner, an embodiment of the invention. In this embodiment, examples of parts of the RF shielding jacket are shown. These parts are used as layers of the RF shielding jacket or modular connecting parts thereof. Further In this embodiment the part (40) has a projection on one side (5) and a fitting socket (6) on the opposite side. The part is perforated (17) from top to bottom on the longitudinal axis of the part. These perforations are used for insulating air pockets and as placements for the transfer of channels, or other parts of an active thermo-regulating system. These perforations are also used for filling with other thermo-regulating materials, enhancing the passive temperature regulating qualities of the RF shielding jacket. Further, these perforations, if used in a single layer RFSJ are configured to RF shield the MRD from EMI by maintaining the relative measurements of the width and diameter of these perforations in reference to the frequency of EMI they are shielding from.

Reference is now made to FIG. 11B schematically illustrating, in an out of scale manner, an embodiment of the invention. In this embodiment, examples of parts of the RF shielding jacket are shown. This part (40) is used as layers of the RF shielding jacket or modular connecting parts thereof. The part is perforated (18) from back to front on the horizontal axis of the part. These perforations are used for insulating air pockets and as placements for the transfer of channels, or other parts of an active thermo-regulating system. These perforations are also used for filling with other thermo-regulating materials, enhancing the passive thermo-regulating qualities of the RF shielding jacket. Further, these perforations, if used in a single layer RFSJ are configured to RF shield the MRD from EMI by maintaining the relative measurements of the width and diameter of these perforations in reference to the frequency of EMI they are shielding from.

Reference is now made to FIG. 12 schematically illustrating, in an out of scale manner, an embodiment of the invention. In this embodiment, an example of a part of the RFSJ is shown. The part (40) is used as a layer of the RF shielding jacket, comprising multiple corrugations and harbors a placement for a liquid, gel, gas or solid particles container (90).

Figure 13:
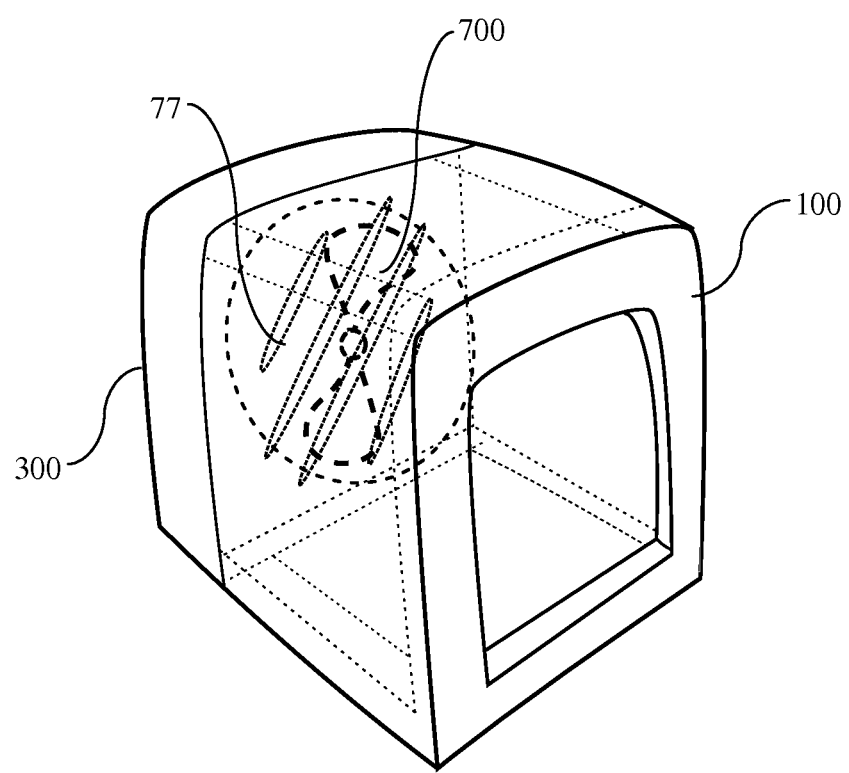
FIG. 13 is a schematic illustration of an MRD thermo isolating jacket embodied as comprising an active thermo-regulating system.

Reference is now made to FIG. 13 schematically illustrating, in an out of scale manner, an embodiment of the invention. In this embodiment, the RF shielding jacket (100) is connected to a detachable thermo-regulating module (300) harboring a vent (700), and openings (77) for the passage of thermo-regulated air.

Figure 14:
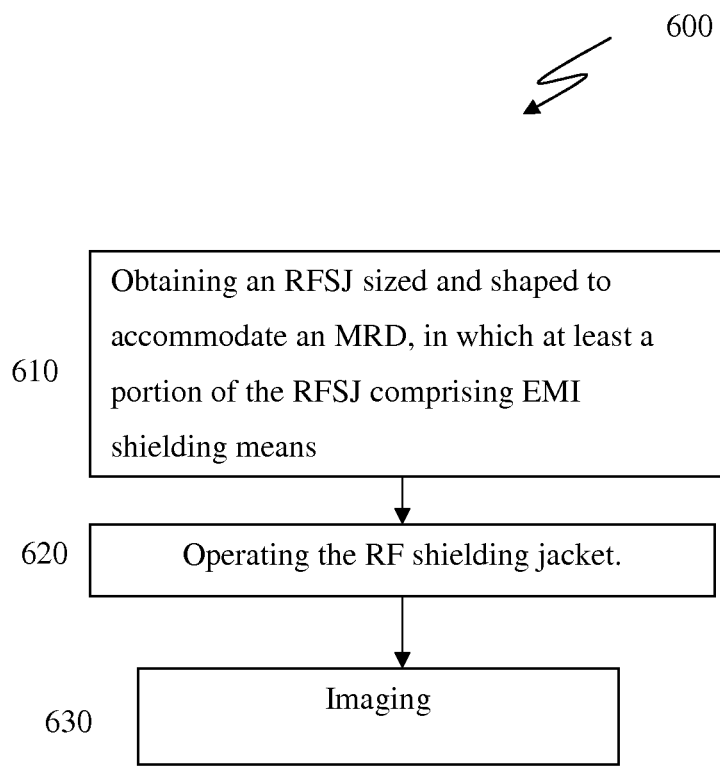
FIG. 14 is a schematic diagram of a method of the current invention describing a block diagram for thermo-regulating an MRD with a RFSJ.

Reference is now made to FIG. 14 schematically describing a flow diagram of a method (600) for RF shielding an MRD, having external dimensions A [m$^2$], and length L0 [m], from electro magnetic interference (EMI). The first step is to obtain an RFSJ sized and shaped to accommodate the MRD (610), in which at least a portion of the RFSJ comprising electromagnetic radiation shielding the MRD from the external environment and contrariwise. The second step is to operate the RFSJ (620) and then image the patient or sample (630).

Figure 15:
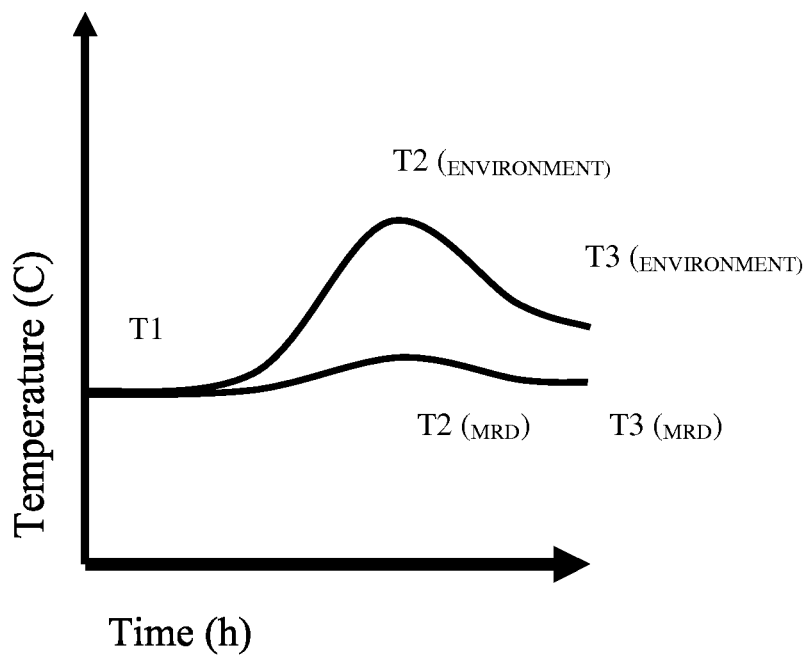
FIG. 15 is a schematic diagram demonstrating the temperature of the environment and the MRD accommodated in a RFSJ as a function of time.

Reference is now made to FIG. 15 schematically illustrating, in an out of scale manner, a schematic diagram demonstrating the temperature of the environment and the MRD accommodated in a RF shielding jacket as a function of time. It is demonstrated that as the environment temperature rises $T1>T2$ ($_{ENVIRONMENT}$) the temperature of the MRD accommodated within the RF shielding jacket rises only to T2 ($_{MRD}$)<T2 ($_{ENVIRONMENT}$).

Figure 16:
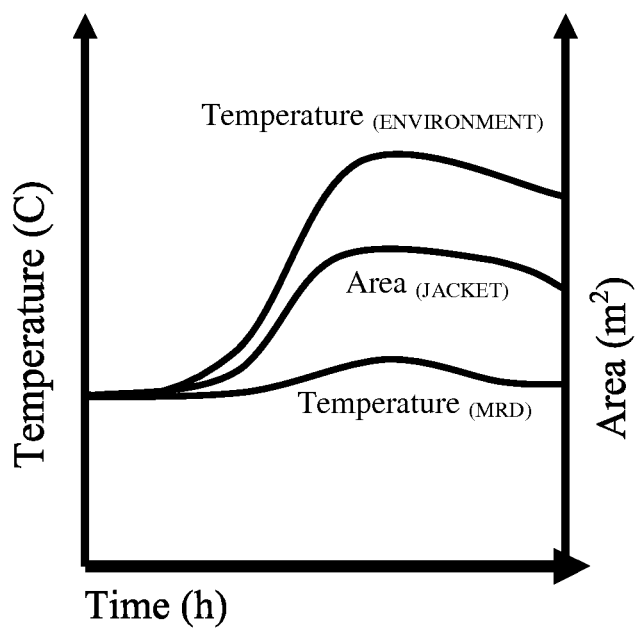
FIG. 16 is a schematic diagram demonstrating the temperature of the environment and the MRD accommodated in RFSJ as a function of time, and the thermal area expansion of a RFSJ during this time rage.

Reference is now made to FIG. 16 schematically illustrating, in an out of scale manner, a schematic diagram demonstrating the temperature of the environment and the MRD accommodated in a RF shielding jacket as a function of time, and the thermal area expansion of a RF shielding jacket during this time rage. As demonstrated the area (m$^2$) of the MRD rises as the temperature of the environment rises, so that the temperature of the MRD accommodated in the RF shielding jacket remains relatively stable.

Figure 17:
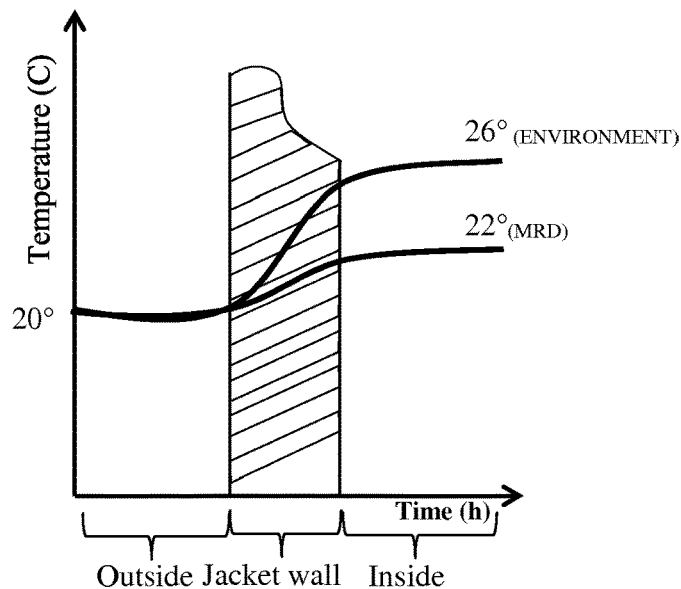
FIG. 17 is a schematic diagram demonstrating the temperature across one section of the RFSJ.

Reference is now made to FIG. 17 schematically illustrating, in an out of scale manner, a schematic diagram demonstrating the temperature across one section of the RF shielding jacket; It is demonstrated that as the environment temperature rises to e.g. 26° C., the temperature of the MRD accommodated within the RFSJ is e.g. 22° C.

Figure 18:
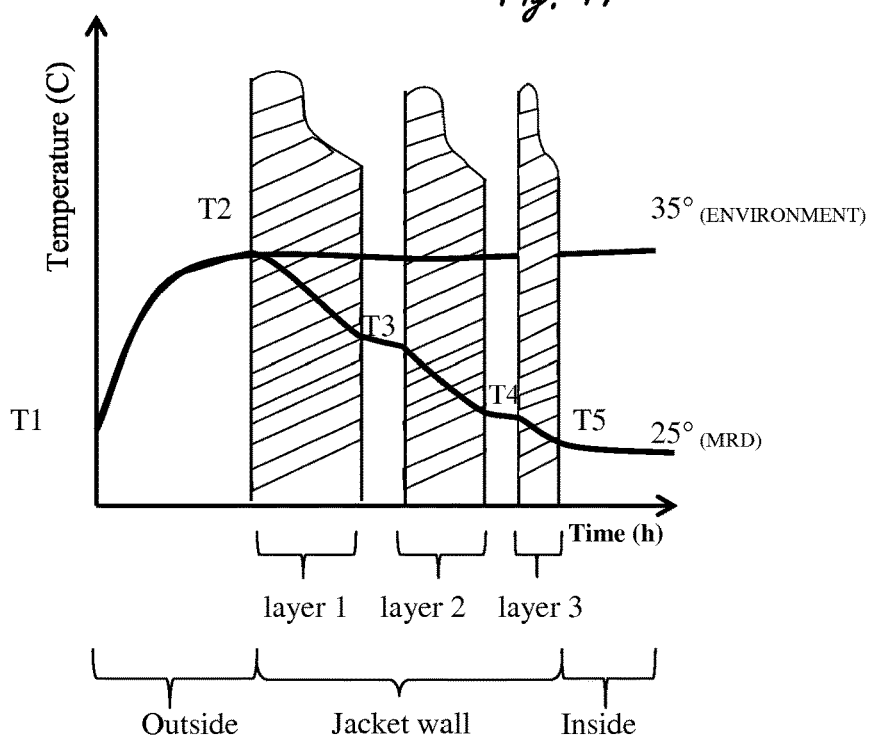
FIG. 18 is a schematic diagram demonstrating the temperature across a section of a layered embodiment of the RFSJ.

Reference is now made to FIG. 18 schematically illustrating, in an out of scale manner, a schematic diagram demonstrating the temperature across a section of a layered embodiment of the RF shielding jacket; It is demonstrated that as the temperature of the environment rises the temperature within the different layers of the RF shielding jacket. For example it is shown that T2>T3>T4>T5; e.g. T2=35° C., T5=25° C.

What is claimed is:

1. An RF shielding jacket (RFSJ), useful for shielding a magnetic resonance device (MRD) having external dimensions A $[m]^2$, and length $L_0$ [m], from electromagnetic interference (EMI), comprising:
   an envelope sized and shaped to accommodate said MRD, wherein at least a portion of said RFSJ comprising an EMI shield; and
   a conduit having a first aperture to a bore of said MRD and a second aperture to an environment external to the RFSJ wherein the conduit has a length to width ratio that prevents radio frequency waves to flow between the bore of said MRD and the environment external to the RFSJ.

2. The RFSJ according to claim 1, wherein at least a portion of said RFSJ comprises means for shielding at least a portion of said MRD from a selected from a group consisting of: magnetism, electromagnetic interference, physical damage and any combination thereof.

3. The RFSJ according to claim 1, wherein said conduit is configured to attenuate the passage of frequencies selected from a group consisting of: 0 to about 1000 MHz, 0 to about 500 MHz, 0 to about 200 MHz and any combination thereof.

4. The RFSJ according to claim 1, wherein said RFSJ comprises an EMI shield configured to attenuate the passage of frequencies selected from a group consisting of: 0 to about 1000 MHz, 0 to about 500 MHz, 0 to about 200 MHz and any combination thereof.

5. The RFSJ according to claim 1, configured for an MRD positioned in an atmospheric pressure system and temperature changing environment, having at least one first temperature $T_1$ [° C.] and a Q [kj] amount of heat applied to the MRD, in which said RFSJ:
   a. at least one second temperature $T_2$ [° C.] in an inner portion of said RFSJ;
   b. a specific mass, m [kg]; and,
   c. specific heat capacity, $C_p$ [kj/kg];
   wherein the following formula is being held true:

$$Q = C_p m dT; \text{ where } dT = T_1 - T_2,$$

wherein for each applied Q, dT2 is in the range of 0° C.-0.2° C.; where $dT2 = T_2 + dT$.

6. The RFSJ according to claim 1, wherein at least a portion of said RFSJ comprising n layers.

7. The RFSJ according to claim 6, wherein at least 2 of said n layers comprising a substantially different specific heat capacity $C_p$ for each layer; where each of said layers has at least one first temperature $H_1$ [° C.] measured on the outer side of said layer, and at least one first temperature $H_2$ [° C.], measured on its inner side towards said MRD, having a $dH_1$-...$dHn$, where dT of RFSJ equals $H_1$-$H_n$.

8. The RFSJ according to claim 6, wherein at least one layer comprising an electrical isolating material.

9. The RFSJ according to claim 6, wherein at least one layer closes a conductive circle around said MRD.

10. The RFSJ according to claim 1, wherein at least a portion of RFSJ comprises a material selected from a group consisting of: thermo insulating material, sealing material, foam material, fire retardant materials, at least partially transparent material and any combination thereof.

11. The RFSJ according to claim 1, wherein at least a portion comprises an active thermos regulating system.

12. The RFSJ according to claim 1, wherein said RFSJ is connected to a component selected from a group consisting of: a CPU, an alarm system, at least one indicator, at least one sensor, and any combination thereof.

13. The RFSJ according to claim 1, configured for an MRD to be positioned in an atmospheric pressure, temperature changing environment, having at least one first temperature $T_1$ [° C.] and at least one second temperature $T_2$ [° C.], in which said RFSJ:
   a. thermal conductivity, k [W/m ° C.];
   b. thickness, s [m]; and,
   c. conductive heat transfer, q [W];
   wherein the following formula is being held true:

$$q = kAdT/s,$$

where dT equals $T_2 - T_1$ and q<<0.01 W.

14. The RFSJ according to claim 1, comprising at least n layers, wherein at least 2 of said n layers comprising a substantially different conductive heat transfer value q for each layer; where each of said layers has at least one first temperature $H_1$ [° C.] measured on the outer side of said layer, and at least one first temperature $H_2$ [° C.], measured on its inner side towards said MRD, having a $dH_1$ ... $dHn$, where dT of said RFSJ equals $H_1$-$Hn$.

15. The RFSJ according to claim 1, in an MRD being positioned in an atmospheric pressure and a temperature changing environment having at least one first temperature $T_1$ [° C.] and at least one second temperature $T_2$ [° C.], a RFSJ for said MRD, wherein said RFSJ is characterized by a thermal expansion coefficient substantially different than 0.

16. The RFSJ according to claim 1, comprising at least n layers, wherein at least 2 of said n layers comprising a substantially different thermal expansion coefficient for each layer; where each of said layers has at least one first temperature $H_1$ [° C.] measured on the outer side of said layer, and at least one first temperature $H_2$ [° C.], measured on its inner side towards said MRD, having a $dH_1$ ... $dHn$, where dT of said RFSJ equals $H_1$-$Hn$.

17. The RFSJ according to claim 16, in which:
   a. length $L_{0, Jacket}$ [m] fitted by means of size and shape to said $L_{0, MRD}$; and
   b. linear thermal expansion coefficient $\alpha_L$ [° C.$^{-1}$] substantially different than 0;
   wherein if dT substantially different than 0; said length $L_{0, Jacket}$ will be varied to $L_{1, Jacket}$, such that the following formula is being held true for any change in temperature, dT:

$$\alpha_L = \frac{1}{L} \frac{dL}{dT}$$

where dL equals $L_{1, Jacket} - L_{0, Jacket}$ and dT equals $T_2 - T_1$.

18. The RFSJ according to claim 16, in which:
   a. volume $V_{0\ Jacket}$ [m]; and,
   b. volumetric thermal expansion coefficient $\alpha_V$ [° C.$^{-1}$] substantially different than 0;
   wherein if dT substantially different than 0; said volume $V_{0, Jacket}$ will be varied to $V_{1, Jacket}$, such that the following formula is being held true for any change in temperature, dT:

$$\alpha_V = \frac{1}{V}\left(\frac{\partial V}{\partial T}\right)$$

where dV equals $V_{1, Jacket} - V_{0, Jacket}$ and dT equals $T_2 - T_1$.

19. The RFSJ according to claim 16, in which:
 a. area $A_{0, Jacket}$ [m²]; and,
 b. area thermal expansion coefficient $\alpha_A$ [° C.$^{-1}$] substantially different than 0;
wherein if dT substantially different than 0; said length $A_{0, Jacket}$ will be varied to $A_{1, Jacket}$, such that the following formula is being held true for any change in temperature, dT:

$$\alpha_A = \frac{1}{A}\frac{dA}{dT}$$

where dA equals $A_{1, Jacket} - A_{0, Jacket}$ and dT equals $T_2 - T_1$.

* * * * *